(12) United States Patent
Chang et al.

(10) Patent No.: US 12,414,396 B2
(45) Date of Patent: Sep. 9, 2025

(54) OPTICAL BIOSENSOR DEVICE WITH OPTICAL SIGNAL ENHANCEMENT STRUCTURE

(71) Applicant: Taiwan Semiconductor Manufacturing Company, Ltd., Hsinchu (TW)

(72) Inventors: Yi-Hsien Chang, Zhubei (TW); Shih-Fen Huang, Jhubei (TW); Chun-Ren Cheng, Hsin-Chu (TW); Fu-Chun Huang, Zhubei (TW); Ching-Hui Lin, Taichung (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 611 days.

(21) Appl. No.: 17/824,183

(22) Filed: May 25, 2022

(65) Prior Publication Data

US 2023/0387164 A1 Nov. 30, 2023

(51) Int. Cl.
*H10F 30/00* (2025.01)
*H10F 39/00* (2025.01)
*H10F 39/12* (2025.01)
*A61B 5/00* (2006.01)

(52) U.S. Cl.
CPC ....... *H10F 39/8063* (2025.01); *H10F 39/024* (2025.01); *H10F 39/198* (2025.01); *H10F 39/8053* (2025.01); *H10F 39/8067* (2025.01); *A61B 5/68* (2013.01); *A61B 2562/146* (2013.01)

(58) Field of Classification Search
None
See application file for complete search history.

(56) References Cited

U.S. PATENT DOCUMENTS

| | | | |
|---|---|---|---|
| 9,366,647 B2 * | 6/2016 | Chang | B01L 3/502707 |
| 9,606,081 B2 | 3/2017 | Chang et al. | |
| 9,968,927 B2 | 5/2018 | Liu et al. | |
| 10,522,400 B2 | 12/2019 | Kalnitsky et al. | |
| 2020/0105996 A1 | 4/2020 | Lin et al. | |

OTHER PUBLICATIONS

Wang et al. "Design and experimental approach of optical reflection filters with graded refractive index profiles" Journal of Vacuum Science & Technology A 17, 206 (1999), published on Jan. 5, 1999.
Ciao et al. "Micromachined polymerase chain reaction system for multiple DNA amplification of upper respiratory tract Infectious diseases" Biosensors and Bioelectronics 20 (2005) 1341-1348, published on Jun. 25, 2004.

(Continued)

*Primary Examiner* — Jyoti Nagpaul
(74) *Attorney, Agent, or Firm* — Eschweiler & Potashnik, LLC

(57) ABSTRACT

The present disclosure relates to an integrated chip including a semiconductor layer and a photodetector disposed along the semiconductor layer. A color filter is over the photodetector. A micro-lens is over the color filter. A dielectric structure comprising one or more dielectric layers is over the micro-lens. A receptor layer is over the dielectric structure. An optical signal enhancement structure is disposed along the dielectric structure and between the receptor layer and the micro-lens.

20 Claims, 14 Drawing Sheets

(56) References Cited

OTHER PUBLICATIONS

Lee et al. "MEMS-based Temperature Control Systems for DNA Amplification" International Journal of Nonlinear Sciences and Numerical Simulation, vol. 3, published Jan. 2002.
Leviton et al. "Variations in refractive index of color filter glasses" Proc. SPIE 3425, Optical Diagnostic Methods for Inorganic Transmissive Materials, published Oct. 8, 1998.
Chang et al. "Integrated polymerase chain reaction chips utilizing digital microfluidics" Biomed Microdevices (2006) 8:215-225, published on May 20, 2006.
Lee et al. "CMOS Based Optical Focusing Stage With Phase Grating Fresnel Lens" Transducers 2009—2009 International Solid-State Sensors, Actuators and Microsystems Conference, published on Oct. 13, 2009.
Khan et al. "Micro-Reflector Integrated Multichannel μLED Optogenetic Neurostimulator With Enhanced Intensity" Front. Mech. Eng., published on Nov. 9, 2018.
Kang et al. "CMOS Image Sensor Packaging Technology for Automotive Applications" Advanced Microsystems for Automotive Applications (pp. 401-412), published in 2005.
Rhoads et al. "PacBio Sequencing and Its Applications" Genomics Proteomics Bioinformatics 13 (2015) 278-289, published on Nov. 2, 2015.
Martinello et al. "Dual Aperture Photography: Image and Depth from a Mobile Camera" 2015 IEEE International Conference on Computational Photography (ICCP), published on Jul. 30, 2015.
He et al. "Study of focal shift effect in planar GaN high contrast grating lenses" Optics Express 29360, vol. 23, No. 23, published on Nov. 2, 2015.
Bogalecki et al. "Integrated Optical Light Directing Structures in CMOS to Improve Light Extraction Efficiency" 22nd International Conference on Microelectronics, published Dec. 2010.
Guissi, Sofiane. "CMOS Image Sensors (CIS): Past, Present & Future" Published on Jun. 14, 2017.
Agilent. "ELISA" The date of publication is unknown. Retrieved online on Mar. 31, 2022 from https://www.biotek.tw/applications/elisa-and-related-immunoassays.html.
Physics. "Tunable Optical Band Pass Filter" The date of publication is unknown. Retrieved online on Mar. 31, 2022 from https://physics.stackexchange.com/questions/156891/tunable-optical-band-pass-filter.
Aliexpress. "IR coated film filter band pass 850nm laser transmissivity more than 92% black glass filter infrared laser filter IR spectrum" The date of publication is unknown. Retrieved online on Mar. 31, 2022 from https://www.aliexpress.com/item/32864007904.html.
Edmound Optics. "Advantages of Fresnel Lenses" The date of publication is unknown. Retrieved online on Mar. 31, 2022 from https://www.edmundoptics.de/knowledge-center/application-notes/optics/advantages-of-fresnel-lenses/.
LED. "LED Lighting Requires New Approaches in Optics" Published on Oct. 22, 2018.
Auer Lighting. "LED Reflectors" The date of publication is unknown. Retrieved online on May 24, 2022 from https://www.auer-lighting.com/en/products/mirrors/led-reflectors.
Abcam. "ELISA principles and types" The date of publication is unknown. Retrieved online on May 24, 2022 from https://www.abcam.com/kits/elisa-principle.
CD Genomics Blog. "Principle and Workflow of Illumina Next-generation Sequencing" Published on Oct. 17, 2018.
Xintec. "Optical Sensor CSP." The date of publication is unknown. Retrieved online on May 24, 2022 from https://www.kintec.com.tw/chi/PS_Optical-Sensor-CSP.aspx.
Science Direct. "Real Time Polymerase Chain Reaction" Food Toxicants Analysis, published in 2007.
Science Direct. "Ion Semiconductor Sequencing" Genomics of Rare Diseases, published in 2021.

\* cited by examiner

OPTICAL BIOSENSOR DEVICE WITH OPTICAL SIGNAL ENHANCEMENT STRUCTURE

BACKGROUND

In recent years, the semiconductor industry has developed integrated chips (ICs) having integrated bio-sensors configured to detect the presence of certain bio-markers in a sample solution (e.g., in a patient's blood). Bio-sensors are analytical devices that convert a biological response into an electrical signal. For example, bio-sensors can generate electrical signals that identify and detect different analytes such as toxins, hormones, DNA strands, proteins, bacteria, etc., in a variety of applications such as molecular diagnostics, pathogen detection, and environmental monitoring. The integration of bio-sensors in system-on-chips (SOCs) provides for promising avenues in the development of diagnostic tools for infectious diseases and cancers.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
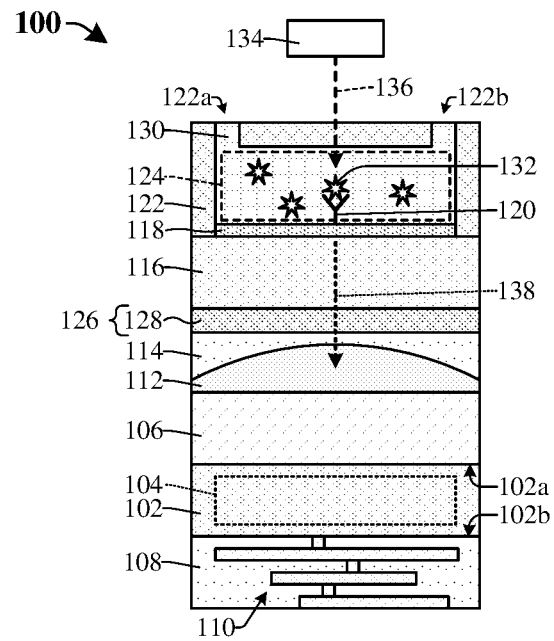
FIGS. 1-5 illustrate cross-sectional views of some embodiments of an optical biosensor integrated chip including a receptor layer disposed directly over a photodetector and an optical signal enhancement structure disposed between the receptor layer and the photodetector.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Optical biosensor devices include elements for detecting an analyte using optical radiation. For example, some optical biosensors include an optical radiation source (e.g., a laser light source), an optical apparatus (e.g., including a lens, a mirror, an optical prism, or the like), a bioreaction device (e.g., a biosensing interface having bioreceptors disposed thereon), and an image sensor (e.g., a photodetector or the like). In some optical biosensors, each of the optical radiation source, the optical apparatus, the bioreaction device, and the image sensor are separate devices assembled together as part of a larger apparatus. A challenge with these optical biosensor devices is that they are typically large, bulky, and/or unportable.

Various embodiments of the present disclosure are related to an optical biosensor device comprising a bioreaction device integrated with an image sensor for improving a portability of the optical biosensor device. For example, the optical biosensor device includes a photodetector disposed along the semiconductor layer. A color filter is disposed over the photodetector. A micro-lens is disposed over the color filter. A dielectric structure is disposed over the micro-lens. A receptor layer is disposed over the dielectric structure. The receptor layer is configured to receive bioreceptors. An optical signal enhancement structure is disposed along the dielectric structure and between the receptor layer and the micro-lens. During operation, a sample solution comprising analytes is provided to bioreceptors which are immobilized along the receptor layer. The bioreceptors are configured to immobilize the analytes. Further, an optical radiation source is configured to excite a bioreaction between the bioreceptors and the analytes with incident optical radiation. The photodetector is configured to detect a sensor optical radiation signal that is emitted from the bioreaction in response to the excitation.

By integrating the bioreaction device and the image sensor into an integrated chip having a small form factor, the size of the optical biosensor device may be reduced and the portability of the optical biosensor device may be improved. Further, by including the optical signal enhancement structure between the receptor layer and the micro-lens, a performance of the optical biosensor device may be improved. For example, the optical signal enhancement structure is configured to enhance the sensor optical radiation signal before the sensor optical radiation signal reaches the photodetector. Thus, a performance (e.g., a sensitivity, an accuracy, etc.) of the optical biosensor device may be improved.

FIG. 1 illustrates a cross-sectional view 100 of some embodiments of an optical biosensor integrated chip including a receptor layer 118 disposed directly over a photodetector 104 and an optical signal enhancement structure 126 disposed between the receptor layer 118 and the photodetector 104.

The photodetector 104 is disposed within a semiconductor layer 102. The semiconductor layer 102 has a frontside 102a and a backside 102b, opposite the frontside 102a. An interlayer dielectric (ILD) structure 108 comprising one or more ILD layers is disposed on the backside 102b of the semiconductor layer 102. An interconnect structure 110 comprising one or more conductive features (e.g., metal lines, vias, contacts, bond pads, etc.) is disposed within the ILD structure 108. In some embodiments, one or more of the conductive features are coupled to the photodetector 104.

A color filter 106 is disposed on the frontside 102a of the semiconductor layer 102. A micro-lens 112 is disposed over the color filter 106. A glue layer 114 is disposed over the micro-lens 112. A dielectric structure 116 is disposed over the glue layer 114. In some embodiments, the glue layer 114 is directly over the micro-lens 112 and directly between the micro-lens 112 and the dielectric structure 116. In some other embodiments, the glue layer 114 is disposed on opposite sides of the color filter 106 and the micro-lens 112 and directly between the semiconductor layer 102 and the dielectric structure 116, but not directly over the micro-lens 112. In some embodiments, a cavity (not shown) comprising air or the like exists directly over the micro-lens 112 and directly between the micro-lens 112 and the dielectric structure 116. In some embodiments, some other suitable optimal material can be disposed directly over the micro-lens 112 and directly between the micro-lens 112 and the dielectric structure 116. The receptor layer 118 and a capping layer 122 are disposed over the dielectric structure 116. A microfluidic channel 124 exists within the capping layer 122. The microfluidic channel 124 is delimited by sidewalls and a lower surface of the capping layer 122. The capping layer 122 has an inlet 122a and an outlet 122b to the microfluidic channel 124. The receptor layer 118 is disposed along the microfluidic channel 124 between the sidewalls of the capping layer 122 and below the lower surface of the capping layer 122 that delimit the microfluidic channel 124. In some embodiments, an upper surface of the receptor layer 118 further delimits the microfluidic channel 124.

In some embodiments, the receptor layer 118 is configured to receive a bioreceptor 120 (e.g., an antibody, an enzyme, a nucleic acid, DNA, etc.). For example, in some embodiments, the receptor layer 118 is configured to immobilize a bioreceptor 120. In some embodiments, a bioreceptor 120 is disposed (e.g., immobilized) along a top of the receptor layer 118. The bioreceptor 120 is configured to receive an analyte 132. For example, the bioreceptor 120 is configured to immobilize an analyte 132. In some instances, a bioreaction occurs when an analyte 132 is immobilized on a bioreceptor 120.

In some embodiments, during operation of the optical biosensor integrated chip, a sample solution 130 comprising one or more analytes 132 is provided to the microfluidic channel 124 via the inlet 122a. An optical radiation source 134 (e.g., a laser light source or some other optical radiation source) emits incident optical radiation 136 toward the optical biosensor integrated chip. In some instances, when an analyte 132 is immobilized on a bioreceptor 120 and the incident optical radiation 136 impinges on the analyte 132 and/or the bioreceptor 120, the bioreaction between the analyte 132 and the bioreceptor 120 emits a sensor optical radiation signal 138. The sensor optical radiation signal 138 passes through the dielectric structure 116, the glue layer 114, the micro-lens 112, and the color filter 106 and impinges on the photodetector 104. The photodetector 104 is configured to detect the sensor optical radiation signal 138. The analyte 132 can be determined based on the detected sensor optical radiation signal 138. For example, a signal processor (not shown) can be coupled to the photodetector 104 and can determine the analyte 132 based on the output of the photodetector 104.

Because the optical biosensor comprises a bioreaction device (e.g., the receptor layer 118 and/or the bioreceptor 120) and an image sensor (e.g., the photodetector 104) implemented in an integrated chip having a small form factor, a portability of the biosensor may be improved.

Further, the biosensor integrated chip includes the optical signal enhancement structure 126 disposed between the receptor layer 118 and the photodetector 104. The optical signal enhancement structure 126 is disposed along the dielectric structure 116 and between the receptor layer 118 and the micro-lens 112. The optical signal enhancement structure 126 comprises one or more elements configured to enhance the sensor optical radiation signal 138 before the sensor optical radiation signal 138 reaches the photodetector 104. For example, in some embodiments, the optical signal enhancement structure 126 is configured to increase an intensity of the sensor optical radiation signal 138 and/or reduce a noise in the sensor optical radiation signal 138, thereby improving a signal-to-noise ratio (SNR) of the sensor optical radiation signal 138. Thus, a performance of the optical biosensor may be improved.

In some embodiments, the optical signal enhancement structure 126 comprises an incident radiation filter layer 128 disposed on a bottom surface of the dielectric structure 116 between the dielectric structure 116 and the glue layer 114. The incident radiation filter layer 128 is disposed and directly over the micro-lens 112 and directly between the micro-lens and the receptor layer 118. In some embodiments, the incident radiation filter layer 128 is configured to block the incident optical radiation 136 from impinging on the photodetector 104. For example, in some embodiments, the incident radiation filter layer 128 is configured to filter (e.g., attenuate) the incident optical radiation 136 and/or some noise radiation (e.g., ambient optical radiation, some other optical background noise, or the like). Thus, a noise (e.g., the incident optical radiation 136, ambient optical radiation, some other optical background noise, or the like) detected by the photodetector 104 may be reduced and hence a performance of the optical biosensor integrated chip may be improved.

In some embodiments, the semiconductor layer 102 may, for example, comprise silicon or some other suitable material. In some embodiments, the photodetector 104 may, for example, be or comprise a photodiode, a complementary metal-oxide-semiconductor (CMOS) image sensor, an avalanche photodiode (APD), a single photon avalanche diode (SPAD) a charge coupled device (CCD), an ion-sensitive field-effect transistor, an infrared photodetector, or the like. In some embodiments, the glue layer 114 may, for example, comprise a material having a high optical transmission rate. In some embodiments, the glue layer 114 may, for example, comprise an epoxy or some other suitable material. In some embodiments, the incident radiation filter layer 128 may, for example, comprise a stack of various films having different refractive indices or some other suitable material(s). In some embodiments, the incident radiation filter layer 128 may be or comprise an infrared (IR) radiation filter layer, a near infrared (NIR) radiation filter layer, or the like. In some embodiments, the dielectric structure 116 comprises a dielectric that is substantially optically transparent to the optical radiation emitted by the bioreaction during the operation of the optical biosensor (e.g., the sensor optical radiation signal 138). In some embodiments, the dielectric structure 116 may, for example, comprise glass, quartz, some plastic material, or some other suitable material. In some embodiments, the receptor layer 118 may, for example, comprise a self-assembled monolayer (SAM), a hydrogel layer, a hydrophilic layer, or some other suitable material. In some embodiments, the capping layer 122 may, for example, comprise glass, quartz, polydimethylsiloxane (PDMS), polymethyl methacrylate (PMMA), some plastic material, or some other suitable material. In some embodiments, the capping layer 122 may be or comprise an electrowetting-on-dielectric (EWOD) microfluidic device, a dielectrophoresis microfluidic device, or some other suitable microfluidic device. In some embodiments, the capping layer 122 may comprise a microfluidic pump (e.g., for pumping the sample solution 130 into the microfluidic channel 124), a valve (e.g., for controlling a flow of the sample solution 130), a microfluidic mixer, or some other suitable microfluidic device components.

Figure 2:
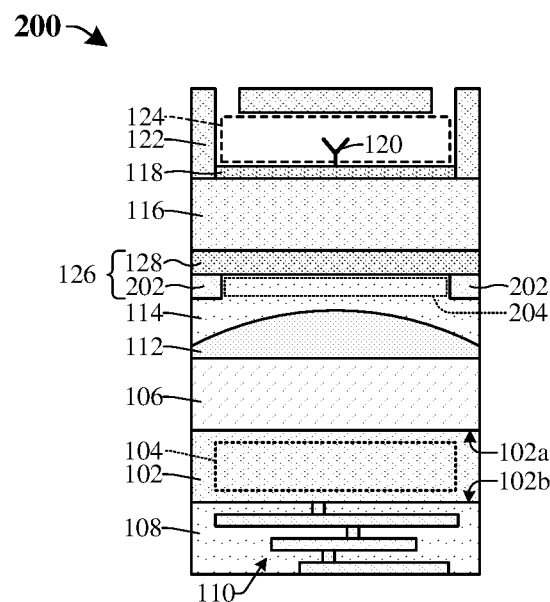

FIG. 2 illustrates a cross-sectional view 200 of some embodiments of the optical biosensor integrated chip of FIG. 1 in which the optical signal enhancement structure 126 additionally or alternatively comprises an aperture layer 202.

In some embodiments, the aperture layer 202 is disposed along a bottom surface of the dielectric structure 116 and a top surface of the glue layer 114. For example, in some embodiments, the aperture layer 202 is disposed on a bottom surface of the incident radiation filter layer 128 and directly between portions of the glue layer 114 and portions of the incident radiation filter layer 128. One or more sidewalls of the aperture layer 202 delimit an aperture 204 in the aperture layer 202. For example, in some embodiments (e.g., where the aperture 204 is circular-shaped when viewed from above), the aperture 204 is delimited by a curved sidewall of aperture layer 202 that extends in a circular shape. In some embodiments (e.g., where the aperture 204 is square-shaped or has some other shape when viewed from above), the aperture 204 is delimited by a plurality of sidewalls of the aperture layer 202 (e.g., four sidewalls in embodiments where the aperture 204 is square shaped). In some embodiments (e.g., when the aperture layer 202 is viewed in cross-section), the aperture 204 is delimited by a pair of sidewalls of the aperture layer 202.

In some embodiments, a portion of the glue layer 114 extends directly between the one or more sidewalls of the aperture layer 202 that delimit the aperture 204. The portion of the glue layer 114 fills the aperture 204. The portion of the glue layer is directly over the micro-lens 112 and directly between the micro-lens 112 and the receptor layer 118. In some embodiments, the portion of the glue layer 114 is directly between the micro-lens 112 and the bioreceptor 120.

In some embodiments, the aperture layer 202 is configured to limit the optical radiation that can pass through to the photodetector 104. For example, some optical radiation may be able to pass through the aperture 204 in the aperture layer 202 but not through the aperture layer 202 itself. In some embodiments, the aperture layer 202 can reduce a crosstalk between the photodetector 104 and neighboring photodetectors (not shown). For example, the aperture layer 202 can block optical radiation from a periphery of the photodetector 104 where the photodetector 104 borders the neighboring photodetectors, thereby reducing a likelihood of crosstalk occurring between the photodetector 104 and the neighboring photodetectors. Thus, a performance of the optical biosensor may be improved. Further, in some embodiments, the aperture layer 202 can block some undesired optical radiation (e.g., the incident optical radiation 136, some ambient optical radiation, some other optical background noise, or the like) from reaching the photodetector 104 which may reduce a noise in the radiation signal detected by the photodetector 104 (e.g., the sensor optical radiation signal 138) and hence improve a SNR of the detected radiation signal.

In some embodiments, the aperture layer 202 may, for example, comprise aluminum, titanium, titanium nitride, or some other suitable material. In some embodiments, a thickness of the aperture layer 202 ranges from about 100 angstroms to 5000 angstroms or some other suitable range.

Figure 3:
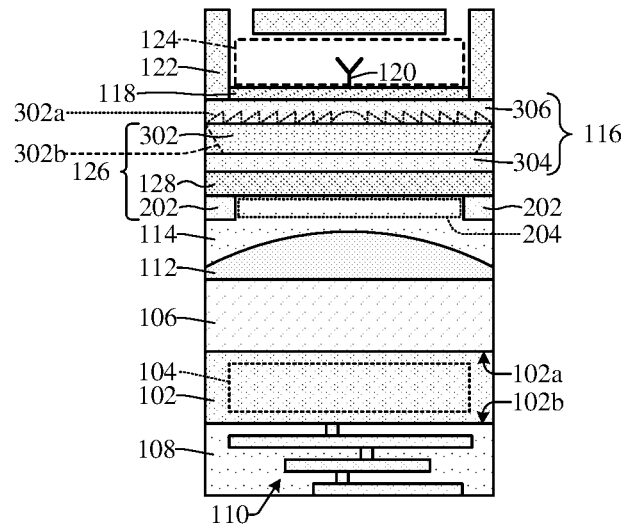

FIG. 3 illustrates a cross-sectional view 300 of some embodiments of the optical biosensor integrated chip of FIG. 2 in which the optical signal enhancement structure 126 additionally or alternatively comprises a focusing layer 302.

The focusing layer 302 is disposed within the dielectric structure 116 directly over the micro-lens 112. For example, in some embodiments, the dielectric structure 116 comprises a first dielectric layer 304 and a second dielectric layer 306 over the first dielectric layer 304. Further, the focusing layer 302 is disposed over the first dielectric layer 304 and the second dielectric layer 306 is disposed over the focusing layer 302. In some embodiments, the focusing layer 302 comprises a material having a suitable refractive index (n) and a suitable extinction coefficient (k). In some embodiments, the focusing layer 302 may, for example, comprise amorphous silicon, silicon nitride, or some other suitable material.

In some embodiments, the focusing layer 302 has a plurality of ring-shaped protrusions (e.g., as shown in the top view 800a illustrated in FIG. 8A and as shown by dashed line 302a of FIG. 3) along a top surface of the focusing layer 302. For example, in some embodiments, the protrusions of focusing layer 302 are similar to those of a Fresnel lens, a grating lens, or the like. The focusing layer 302 is configured to focus the sensor optical radiation signal (e.g., 138 of FIG. 1) to enhance the sensor optical radiation signal. For example, in some embodiments, the focusing layer 302 is configured to increase the intensity of the sensor optical radiator signal before the sensor optical radiation signal reaches, and is detected by, the photodetector 104. Thus, the focusing layer 302 may improve the SNR of the sensor optical radiation signal and hence the performance of the optical biosensors may be improved. In some embodiments, the shape and pitch of the ring-shaped protrusions (e.g., illustrated by dashed line 302a) may be adjusted to tune the focus of the focusing layer 302.

In some other embodiments, sidewalls of the focusing layer 302 are configured to reflect radiation (e.g., the sensor optical radiation signal 138 of FIG. 1) toward the photodetector 104 to increase an intensity of the radiation. For example, the focusing layer 302 may be or function as a light pipe or a light channel. Thus, the focusing layer 302 may improve the SNR of the signal received by the photodetector 104 (e.g., the sensor optical radiation signal 138 of FIG. 1) and hence may improve a performance of the photodetector 104. Further, in some embodiments, the sidewalls of the focusing layer 302 may reflect radiation toward the photodetector 104 that is directly under the focusing layer 302 and away from neighboring photodetectors (not shown) that are not directly under the focusing layer 302 to reduce a crosstalk between the underlying photodetector 104 and the neighboring photodetectors. In some embodiments, the sidewalls of the focusing layer 302 are slanted (e.g., as shown by dashed lines 302b) such that a distance between the sidewalls along the tops of the sidewalls is greater than a distance between the sidewalls along the bottoms of the sidewalls. The slanting of the sidewalls may be controlled to tune the angle of reflection of the radiation to further increase the intensity of the radiation that is reflected toward the photodetector 104.

Figure 4:
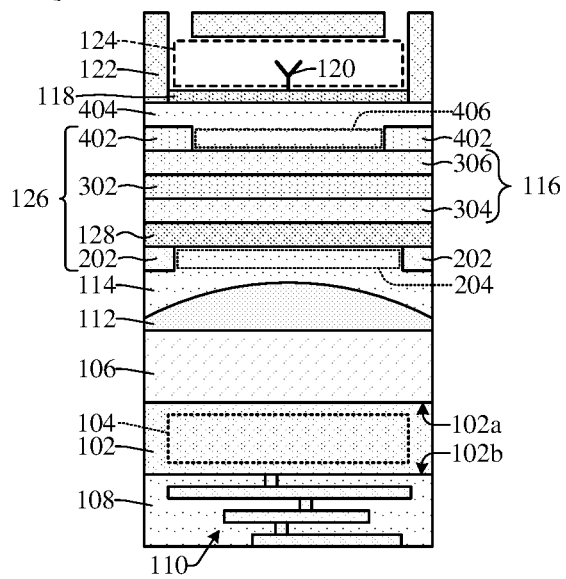

FIG. 4 illustrates a cross-sectional view 400 of some embodiments of the optical biosensor integrated chip of FIG. 3 in which the optical signal enhancement structure 126 additionally or alternatively comprises a reflector layer 402.

The reflector layer 402 is disposed along a top surface of the dielectric structure 116. One or more sidewalls of the reflector layer 402 delimit an aperture 406 in the reflector layer 402. In some embodiments (e.g., when the reflector layer 402 is viewed in cross-section), the aperture 406 is delimited by a pair of sidewalls of the reflector layer 402. A first clad layer 404 is disposed over the reflector layer 402. In some embodiments, a portion of the first clad layer 404 extends directly between the sidewalls of the reflector layer 402 that delimit the aperture 406. The portion of the first clad layer 404 fills the aperture 406. The portion of the first clad layer 404 is directly over the micro-lens 112 and directly between the micro-lens 112 and the receptor layer 118. In some embodiments, the portion of the first clad layer 404 is on the top surface of the dielectric structure 116. In some embodiments, the portion of the first clad layer 404 is directly between the micro-lens 112 and the bioreceptor 120.

In some embodiments, the reflector layer 402 is configured to reflect noise radiation (e.g., the incident optical radiation 136, some ambient optical radiation, some other optical background noise, or the like) while allowing the sensor optical radiation signal 138 to pass through at the apertures 406. As a result, an SNR of the sensor optical radiation signal 138 may be improved and hence a performance of the optical biosensor may be improved. In some embodiments, by including the reflector layer 402 over the focusing layer 302 such that the aperture 406 is directly over the focusing layer 302, the noise radiation may be blocked from the focusing layer 302 without blocking the sensor optical radiation signal 138, thereby reducing the likelihood that the noise radiation will be intensified and focused on the photodetector 104 by the focusing layer 302.

In some embodiments, the reflector layer 402 may, for example, comprise aluminum, titanium, titanium nitride, chromium, or some other suitable material. In some embodiments, the reflector layer 402 comprises a different material than the aperture layer 202. In some embodiments, a thickness of the reflector layer 402 ranges from about 100 angstroms to 2000 angstroms or some other suitable range. In some embodiments, the thickness of the reflector layer 402 is less than the thickens of the aperture layer 202. In some embodiments, the aperture 406 in the reflector layer 402 is smaller than the aperture 204 in the aperture layer 202. For example, when viewed in cross-section, a distance between the sidewalls of the reflector layer 402 that delimit the aperture 406 is less than a distance between the sidewalls of the aperture layer 202 that delimit the aperture 204. In some embodiments, the first clad layer 404 may, for example, comprise a low-k dielectric (e.g., silicon dioxide or the like) or some other suitable material.

Figure 5:
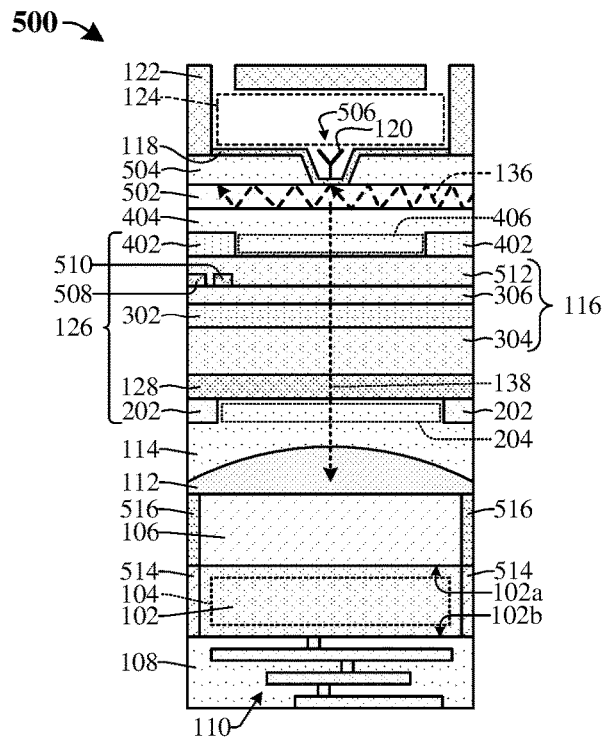

FIG. 5 illustrates a cross-sectional view 500 of some embodiments of the optical biosensor integrated chip of FIG. 4 in which a waveguide channel core layer 502 is disposed between the optical signal enhancement structure 126 and the receptor layer 118.

The waveguide channel core layer 502 is disposed over the first clad layer 404 and a second clad layer 504 is disposed over the waveguide channel core layer 502. Sidewalls of the second clad layer 504 and an upper surface of the waveguide channel core layer 502 delimit a bioreaction chamber 506. The bioreaction chamber 506 is directly over the photodetector 104. In some embodiments, the receptor layer 118 lines the sidewalls of the second clad layer 504 and the upper surface of the waveguide channel core layer 502 and the receptor layer 118 further delimits the bioreaction chamber 506. In some embodiments, the bioreceptor 120 is disposed along the receptor layer 118 directly between the sidewalls of the second clad layer 504 and directly over the upper surface of the waveguide channel core layer 502.

In some embodiments, the incident optical radiation 136 travels along the waveguide channel core layer 502 to the bioreaction chamber 506 by way of total internal reflection. The incident optical radiation impinges on the bioreceptor 120 at the bioreaction chamber 506 to excite a bioreaction at the bioreceptor 120. The bioreaction may then emit the sensor optical radiation signal 138 which the photodetector 104 is configured to detect.

In some embodiments, a temperature sensor 508 and/or a heater 510 are disposed within the dielectric structure 116. For example, in some embodiments, the dielectric structure 116 includes the first dielectric layer 304, the second dielectric layer 306 over the first dielectric layer 304, and a third dielectric layer 512 over the second dielectric layer 306. Further, the temperature sensor 508 and the heater 510 are disposed over the second dielectric layer 306 and the third dielectric layer 512 is disposed over both the temperature sensor 508 and the heater 510. The temperature sensor 508 and the heater 510 are respectively configured to detect and control the temperature of the integrated chip and/or the sample solution (e.g., 130 of FIG. 1) injected into the microfluidic channel 124. By detecting and controlling the temperature of the integrated chip and/or the sample solution that is injected into the integrated chip, a performance of the optical biosensor integrated chip may be improved.

In some embodiments, a trench isolation structure 514 is disposed on opposite sides of the photodetector 104 and isolates the photodetector 104 from neighboring photodetectors (not shown). In some embodiments, the trench isolation structure 514 may, for example, comprise a dielectric, a metal, or some other suitable material. In some embodiments, a composite metal grid (CMG) structure 516 is disposed on opposite sides of the color filter 106 and separates the color filter 106 from neighboring color filters (not shown). In some embodiments, the CMG structure 516 is disposed directly over the trench isolation structure 514. In some embodiments, the CMG structure 516 may, for example, comprises a metal and a dielectric or some other suitable material(s).

In some embodiments, the waveguide channel core layer 502 may, for example, comprise a high-k dielectric (e.g., barium strontium titanate (BST), lead zirconate titanate (PZT), tantalum oxide, hafnium oxide, silicon nitride, aluminum oxide) or some other suitable material. In some embodiments, the second clad layer 504 may, for example, comprise a same material as the first clad layer 404. In some other embodiments, the second clad layer 504 may comprise a different low-k dielectric than the first clad layer 404. In some embodiments, the temperature sensor 508 and/or the heater 510 may, for example, comprise platinum, polysilicon, or some other suitable material.

Figure 6:
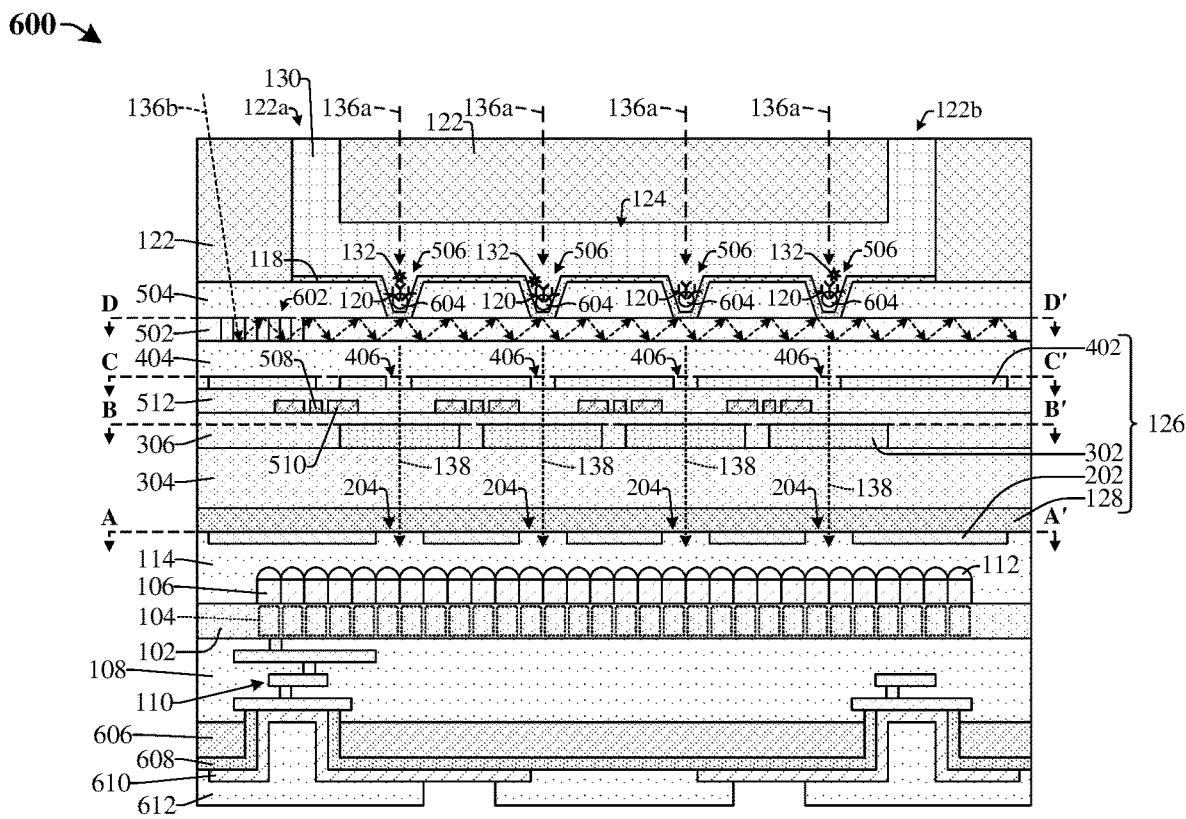
FIG. 6 illustrates a cross-sectional view of some embodiments of an optical biosensor integrated chip including a receptor layer disposed directly over a plurality of photodetectors and an optical signal enhancement structure disposed between the receptor layer and the plurality of photodetectors.

FIG. 6 illustrates a cross-sectional view 600 of some embodiments of an optical biosensor integrated chip including a receptor layer 118 disposed directly over a plurality of photodetectors 104 and an optical signal enhancement structure 126 disposed between the receptor layer 118 and the plurality of photodetectors 104.

A plurality of color filters 106 are disposed over the plurality of photodetectors 104, respectively, and a plurality of micro-lenses 112 are disposed over the plurality of color filters 106, respectively. In some embodiments, the aperture layer 202 comprises a plurality of aperture segments (not labeled) when viewed in cross-section. Sidewalls of the aperture layer 202 delimit a plurality of apertures 204 in the aperture layer 202. In some embodiments, the focusing layer 302 comprises a plurality of focusing layer segments (not labeled). In some embodiments, each of the focusing layer segments has a plurality of ring-shaped protrusions along the top surfaces of the segments. In some other embodiments, the focusing layer segments have slanted sidewalls. In some embodiments, a plurality of temperature sensors 508 and a plurality of heaters 510 are disposed over the second dielectric layer 306 and are laterally spaced apart from one another. In some embodiments, the reflector layer 402 comprises a plurality of reflector segments (not labeled) when viewed in cross-section. Sidewalls of the reflector layer 402 delimit a plurality of apertures 406 in the reflector layer 402.

In some embodiments, the waveguide channel core layer 502 comprises a light coupler structure 602. The light coupler structure 602 is formed by a plurality of segments of the waveguide channel core layer 502. In some embodiments, the waveguide channel core layer 502 further comprises a light splitter structure (not shown) configured to transfer (e.g., split) optical radiation into multiple output waveguide channel core layers from an input waveguide channel core layer.

A plurality of bioreaction chambers 506 are disposed along the second clad layer 504 and the waveguide channel core layer 502. The bioreaction chambers 506 are directly over the apertures 406 in the reflector layer 402, the focusing segments of the focusing layer 302, the incident radiation filter layer 128, and the apertures 204 in the aperture layer 202. Further, the bioreaction chambers 506 are directly over one or more of the micro-lenses 112, one or more of the color filters 106, and one or more of the photodetectors 104. In some embodiments, a plurality of microbeads 604 having bioreceptors 120 disposed thereon are disposed along the receptor layer 118 in the plurality of bioreaction chambers 506, respectively. In some other embodiments, the biosensor is devoid of the microbeads 604 and the bioreceptors 120 are disposed on the receptor layer 118.

In some embodiments, a carrier wafer 606 is disposed below the ILD structure 108. An isolation layer 608 is disposed along a bottom surface and sidewalls of the carrier wafer 606. A through-substrate via (TSV) layer 610 comprising a plurality of separate TSV segments (not labeled) is disposed along sidewalls and a bottom surface of the isolation layer 608. The TSV segments are coupled to conductive features of the interconnect structure 110. The isolation layer 608 isolates the TSV layer 610 from the carrier wafer 606. A passivation layer 612 is disposed on sidewalls and a bottom surface of the TSV layer 610. The passivation layer 612 extends between and isolates TSV segments of the TSV layer 610. Openings in the passivation layer 612 expose portions of the TSV segments of the TSV layer 610.

In some embodiments, bioreactions between the bioreceptors 120 and the analytes 132 are excited by first incident radiation 136a that is emitted directly over the bioreaction chambers 506 and that passes through the capping layer 122 to the bioreaction chambers 506 to excite bioreactions at each of the bioreaction chambers 506. In some other embodiments, bioreactions between the bioreceptors 120 and the analytes 132 are excited by second incident radiation 136b which passes through the capping layer 122 and the second clad layer 504 and impinges on the light coupler structure 602. The second incident radiation 136b then travels along the waveguide channel core layer 502 from the light coupler structure 602 to each of the bioreaction chambers 506. For example, after impinging on the light coupler structure 602, the second incident radiation 136b experiences total internal reflection within the waveguide channel core layer 502 such that photons from the second incident radiation 136b travel along the waveguide channel core layer 502 and impinge on the bioreceptors 120 and analytes 132 at each of the bioreaction chambers 506. The second incident radiation 136b excites bioreactions at each of the bioreaction chambers 506.

In some embodiments, the microbeads 604 may, for example, comprise silicon, silica, polystyrene, copper, a magnetic material, or some other suitable material. In some embodiments, the carrier wafer 606 may, for example, comprise silicon or some other suitable material. In some embodiments, the isolation layer 608 may, for example, comprise silicon dioxide, silicon nitride, or some other suitable material. In some embodiments, the TSV layer 610 may, for example, comprise copper, tungsten, aluminum, or some other suitable material. In some embodiments, the passivation layer 612 may, for example, comprise silicon nitride or some other suitable material.

FIGS. 7, 8A, 8B, 9, and 10 illustrate top views 700, 800a, 800b, 900, 1000 of some embodiments of the optical biosensor integrated chip of FIG. 6.

Figure 7:
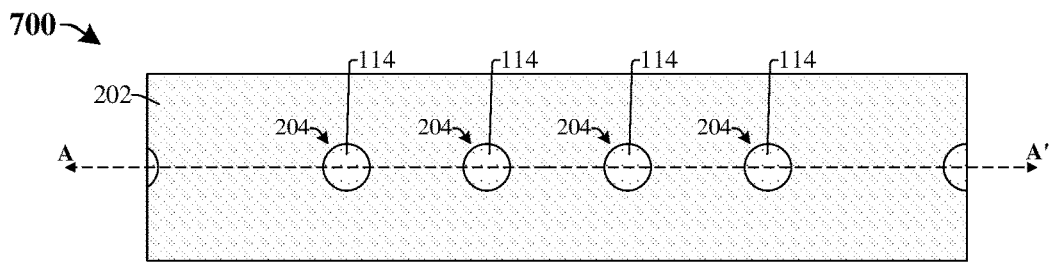
FIGS. 7, 8A, 8B, 9, and 10 illustrate top views of some embodiments of the optical biosensor integrated chip of FIG. 6.

In some embodiments, top view 700 illustrated in FIG. 7 is taken across line A-A' of FIG. 6. In some embodiments, the apertures 204 in the aperture layer 202 are circular-shaped when viewed from above, as illustrated in FIG. 7. In some other embodiments (not shown), the apertures 204 in the aperture layer 202 are square-shaped or have some other shape when viewed from above.

Figure 8A:
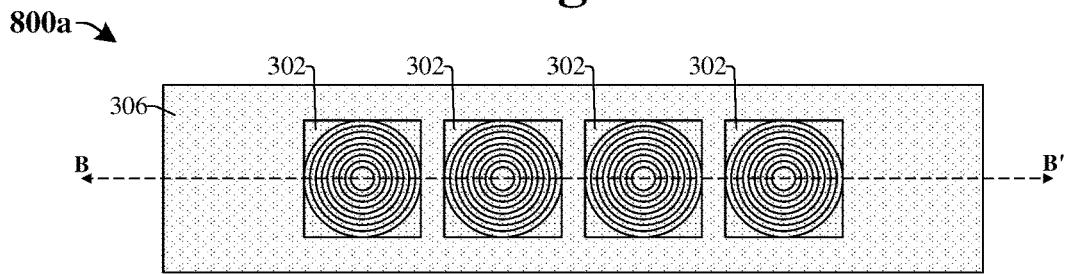
Figure 8B:
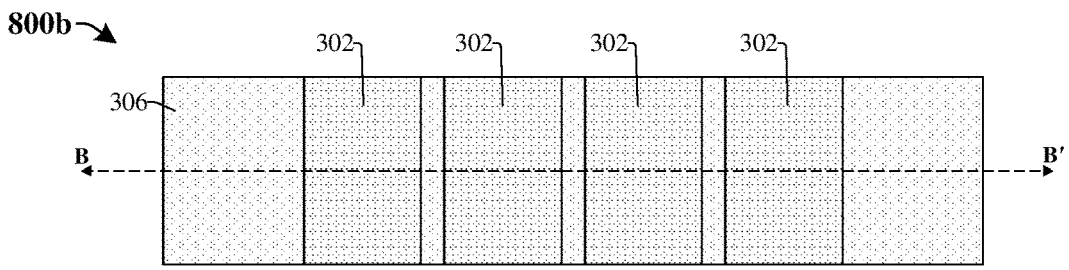

In some embodiments, top views 800a, 800b illustrated in FIGS. 8A and 8B are taken across line B-B' of FIG. 6. In some embodiments (e.g., as illustrated in top view 800a of FIG. 8A), the focusing segments of the focusing layer 302 have a plurality of ring-shaped protrusions along the top surfaces of the segments. In some embodiments, the focusing segments of the focusing layer 302 are square-shaped, circular-shaped, or have some other shape when viewed from above. In some other embodiments (e.g., as illustrated in top view 800b of FIG. 8B), the focusing segments of the focusing layer 302 have substantially planar top surfaces and are square-shaped, rectangular-shaped, or have some other shape.

Figure 9:
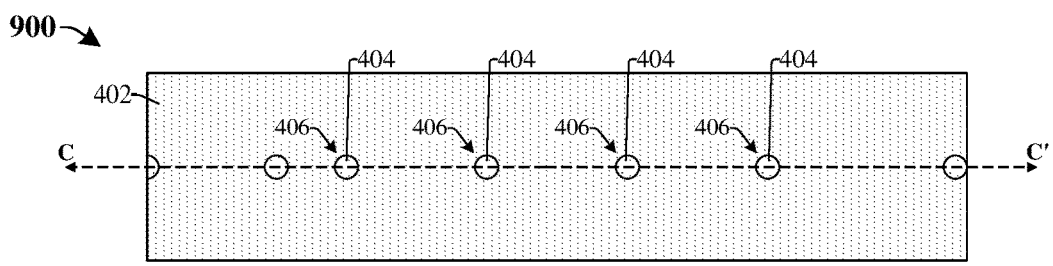

In some embodiments, top view 900 illustrated in FIG. 9 is taken across line C-C' of FIG. 6. In some embodiments, the apertures 406 in the reflector layer 402 are circular-shaped when viewed from above, as illustrated in FIG. 9. In some other embodiments (not shown), the apertures 406 in the reflector layer 402 are square-shaped or have some other shape when viewed from above.

Figure 10:
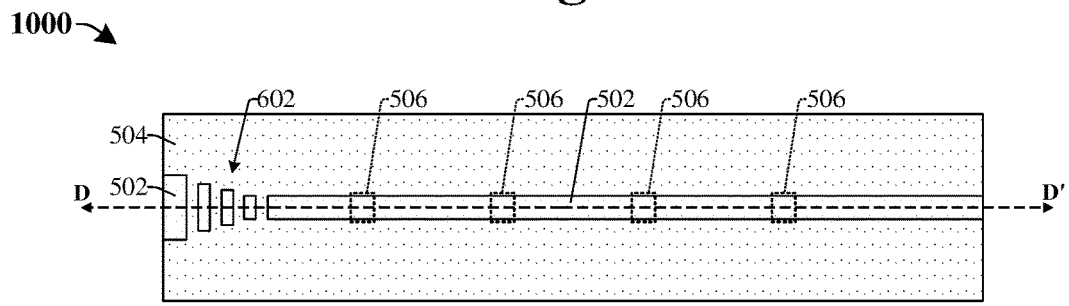

In some embodiments, top view 1000 illustrated in FIG. 10 is taken across line D-D' of FIG. 6. The light coupler structure 602 is formed by a plurality of adjacent segments of the waveguide channel core layer 502. In some embodiments, the segments of the waveguide channel core layer 502 that form the light coupler structure 602 have varying lengths.

FIGS. 11-39 illustrate cross-sectional views 1100-3900 of some embodiments of a method for forming an optical biosensor integrated chip including a receptor layer 118 disposed directly over a photodetector 104 and an optical signal enhancement structure 126 disposed between the receptor layer 118 and the photodetector 104. Although FIGS. 1100-3900 are described in relation to a method, it will be appreciated that the structures disclosed in FIGS. 1100-3900 are not limited to such a method, but instead may stand alone as structures independent of the method.

FIGS. 11-16 illustrate cross-sectional views 1100-1600 of some embodiments of a method for forming an image sensor wafer.

Figure 11:
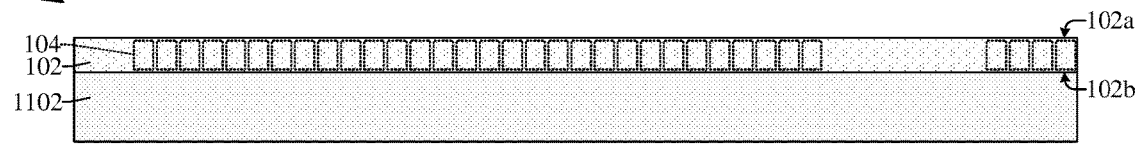
FIGS. 11-39 illustrate cross-sectional views of some embodiments of a method for forming an optical biosensor integrated chip including a receptor layer disposed directly over a photodetector and an optical signal enhancement structure disposed between the receptor layer and the photodetector.

As shown in cross-sectional view 1100 of FIG. 11, a plurality of photodetectors 104 are formed within a semiconductor layer 102 along a frontside 102a of the semiconductor layer 102. In some embodiments, the semiconductor layer 102 is formed on a substrate 1102 before the photodetectors 104 are formed within the semiconductor layer 102.

In some embodiments, forming the plurality of photodetectors 104 comprises performing one or more implantation processes, diffusion processes, or some other suitable processes along the semiconductor layer 102. In some embodiments, the semiconductor layer 102 comprises silicon or some other suitable material and is formed on the substrate 1102 by a chemical vapor deposition (CVD) process, a physical vapor deposition (PVD) process, an atomic layer deposition (ALD) process, an epitaxial growth process, or some other suitable process. In some embodiments, the substrate 1102 comprises silicon, a semiconductor-on-insulator (SOI) stack, or some other suitable material(s).

Figure 12:
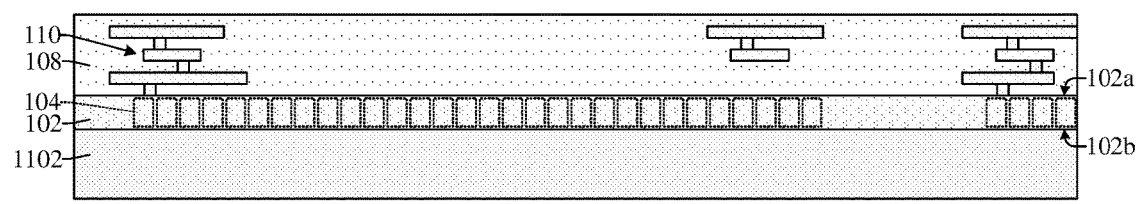

As shown in cross-sectional view 1200 of FIG. 12, an ILD structure 108 is formed over a backside 102b of the semiconductor layer 102, opposite the frontside 102a. Further, an interconnect structure 110 is formed within the ILD structure 108. The interconnect structure 110 comprises a plurality of conductive features disposed within the ILD structure 108.

In some embodiments, the ILD structure 108 comprises silicon oxide, silicon nitride, or some other suitable material and is formed by a CVD process, a PVD process, an ALD process, or some other suitable process. In some embodiments, the conductive features of the interconnect structure 110 comprise copper, tungsten, aluminum, or some other suitable material and are formed within the ILD structure 108 by a CVD process, a PVD process, an ALD process, a sputtering process, an electroless deposition (ELD) process, an electrochemical deposition (ECD) process, or some other suitable process.

Figure 13:
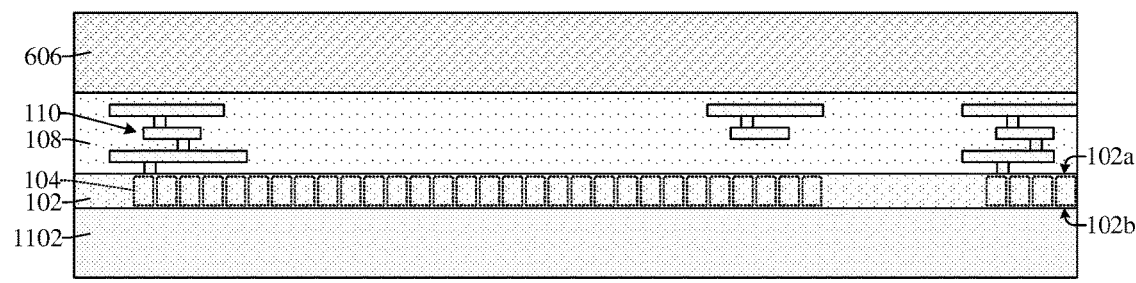

As shown in cross-sectional view 1300 of FIG. 13, a carrier wafer 606 is bonded over the ILD structure 108. For example, in some embodiments, the carrier wafer 606 is bonded to the ILD structure 108 along a first side of the carrier wafer 606. In some other embodiments, the carrier wafer 606 is bonded to a bonding layer (not shown) that is over the ILD structure 108 along the first side of the carrier wafer 606. In some embodiments, the carrier wafer 606 comprises silicon or some other suitable material. In some embodiments, the bonding comprises a fusion boding process, an adhesive bonding process, or some other suitable process.

Figure 14:
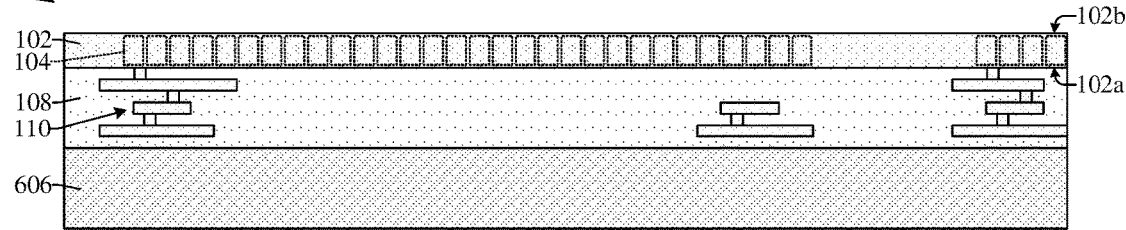

As shown in cross-sectional view 1400 of FIG. 14, the substrate 1102 is removed from the backside 102b of the semiconductor layer 102. In some embodiments, the semiconductor layer 102 is thinned along the backside 102b of the semiconductor layer 102. In some embodiments, the removal of the substrate 1102 from the backside 102b of the semiconductor layer 102 and/or the thinning of the semiconductor layer 102 comprises a chemical mechanical planarization (CMP) process, a grinding process, a blanket etch back process, or some other suitable process.

Figure 15:
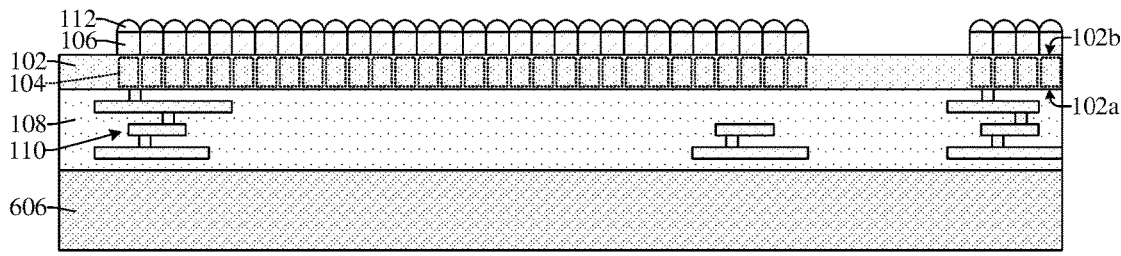

As shown in cross-sectional view 1500 of FIG. 15, a plurality of color filters 106 are formed over the plurality of photodetectors 104, respectively, along the backside 102b of the semiconductor layer 102. In some embodiments, forming the color filters 106 comprises depositing and patterning a plurality of color resist layers over the photodetectors 104. Further, a plurality of micro-lenses 112 are formed directly over the plurality of color filters 106, respectively. In some embodiments, forming the micro-lenses 112 comprises disposing a micro-lens template over a micro-lens material and shaping the micro-lens material according to the micro-lens template.

Figure 16:
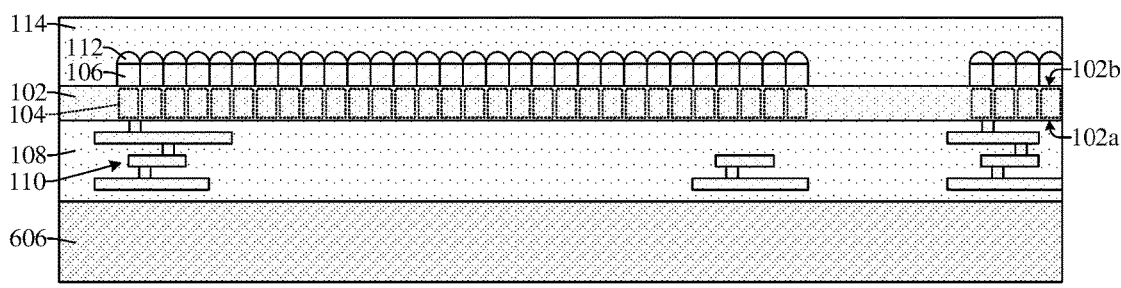

As shown in cross-sectional view 1600 of FIG. 16, a glue layer 114 is deposited over the micro-lenses 112. Further, the glue layer 114 is deposited on opposite sides of the micro-lenses 112 and color filters 106. In some embodiments, the glue layer 114 comprises an epoxy or some other suitable material and is deposited by a spread coating process, a CVD process, a PVD process, an ALD process, or some other suitable process. In some other embodiments, the glue layer 114 may be deposited around a periphery of the color filters 106 and micro-lenses 112 but not directly over the micro-lenses 112.

FIGS. 17-34 illustrate cross-sectional views 1700-3400 of some embodiments of a method for forming a bioreaction wafer.

Figure 17:
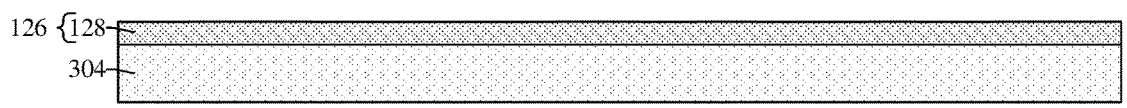

As shown in cross-sectional view 1700 of FIG. 17, an incident radiation filter layer 128 is deposited over a first side of a first dielectric layer 304. In some embodiments, the first dielectric layer 304 comprises glass, quartz, some plastic material, or some other suitable material. In some embodiments, the incident radiation filter layer 128 comprises a stack of various films having different refractive indices or some other suitable material and is deposited by a CVD process, a PVD process, an ALD process, or some other suitable process.

Figure 18:
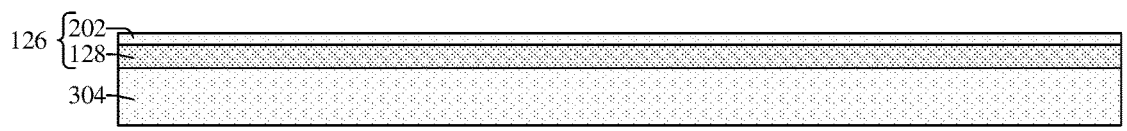

As shown in cross-sectional view 1800 of FIG. 18, an aperture layer 202 is deposited over the incident radiation filter layer 128. In some embodiments, the aperture layer 202 comprises aluminum, titanium, titanium nitride, or some other suitable material and is deposited by a CVD process, a PVD process, an ALD process, a sputtering process, an ELD process, an ECD process, or some other suitable process.

Figure 19:
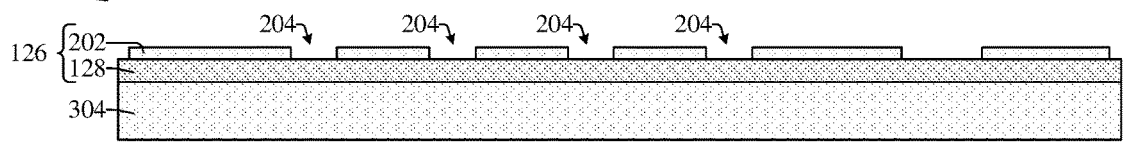

As shown in cross-sectional view 1900 of FIG. 19, the aperture layer 202 is patterned to form a plurality of apertures 204 in the aperture layer 202. The plurality of apertures 204 are delimited by sidewalls of the aperture layer 202. In some embodiments, the patterning comprises forming a masking layer (not shown) over the aperture layer 202 and etching the aperture layer 202 according to the masking layer to form the apertures 204 in the aperture layer 202. In some embodiments, the etching comprises a dry etching process (e.g., a plasma etching process, a reaction ion etching process, an ion beam etching process, or the like) or some other suitable process. In some embodiments, the masking layer may be removed during and/or after the etching.

Figure 20:
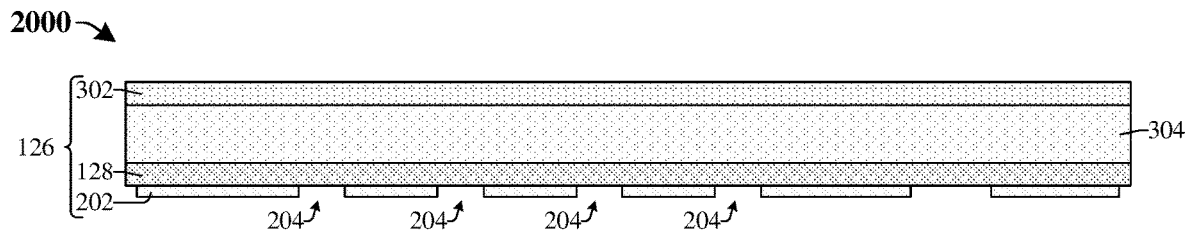

As shown in cross-sectional view 2000 of FIG. 20, a focusing layer 302 is deposited over a second side of the first dielectric layer 304, opposite the first side. In some embodiments, the focusing layer 302 comprises amorphous silicon, silicon nitride, or some other suitable material and is deposited by a CVD process, a PVD process, an ALD process, or some other suitable process.

Figure 21:
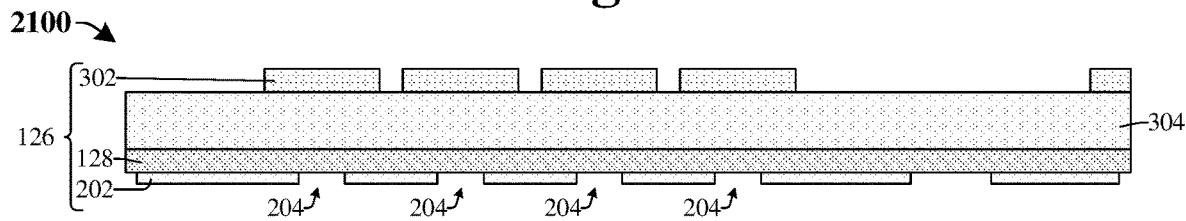

As shown in cross-sectional view 2100 of FIG. 21, the focusing layer 302 is patterned to form a plurality of focusing layer segments (not labeled). In some embodiments, the patterning comprises performing one or more etching processes according to one or more masking layers. In some embodiments, the patterning forms a plurality of protrusions along top surfaces of the focusing layer segments (e.g., as illustrated in FIG. 8A and by dashed line 302a of FIG. 3). In some other embodiments, the patterning may result in the focusing layer segments having slanted sidewalls (e.g., as illustrated by dashed lines 302b of FIG. 3) and/or substantially planar top surfaces (e.g., as illustrated in FIG. 8B).

Figure 22:
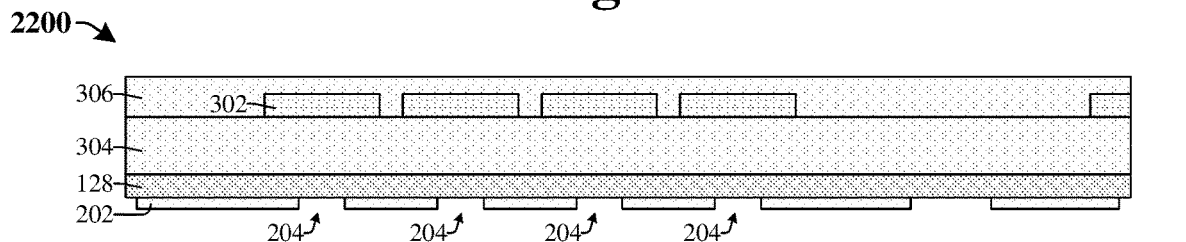

As shown in cross-sectional view 2200 of FIG. 22, a second dielectric layer 306 is deposited over the focusing layer 302 and between the focusing layer segments (not labeled). In some embodiments, the second dielectric layer 306 comprises glass, quartz, some plastic material, or some other suitable material and is deposited by a CVD process, a PVD process, an ALD process, or some other suitable process.

Figure 23:
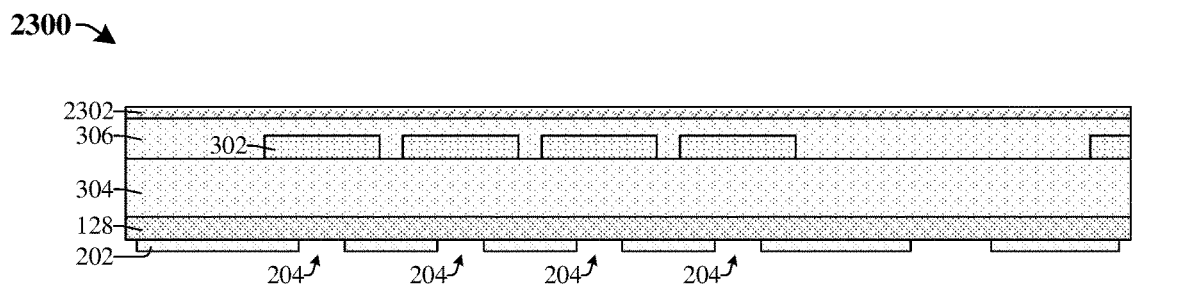

As shown in cross-sectional view 2300 of FIG. 23, a thermal controller layer 2302 is deposited over the second dielectric layer 306. In some embodiments, the thermal controller layer 2302 comprises platinum, polysilicon, or some other suitable material and is deposited by a CVD process, a PVD process, an ALD process, a sputtering process, an ELD process, an ECD process, or some other suitable process.

Figure 24:
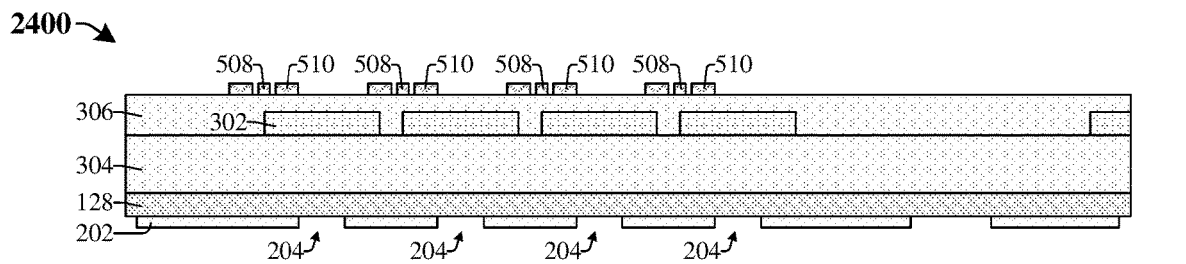

As shown in cross-sectional view 2400 of FIG. 24, the thermal controller layer (e.g., 2302 of FIG. 23) is patterned to form a plurality of temperature sensors 508 and a plurality of heaters 510 from the thermal controller layer. In some embodiments, the patterning comprises forming a masking layer (not shown) over the thermal controller layer and etching the thermal controller layer according to the masking layer to form the temperature sensors 508 and the heaters 510 from the thermal controller layer. In some embodiments, the etching comprises a dry etching process or some other suitable process. In some embodiments, the masking layer may be removed during and/or after the etching.

Figure 25:
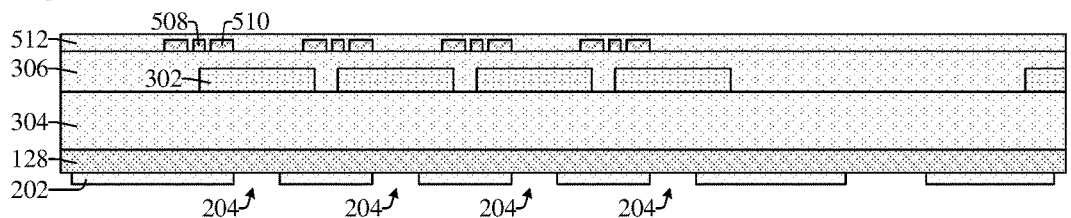

As shown in cross-sectional view 2500 of FIG. 25, a third dielectric layer 512 is deposited over the temperature sensors 508, over the heaters 510, and between the temperature sensors 508 and the heaters 510. In some embodiments, the third dielectric layer 512 comprises glass, quartz, some plastic material, or some other suitable material and is deposited by a CVD process, a PVD process, an ALD process, or some other suitable process.

Figure 26:
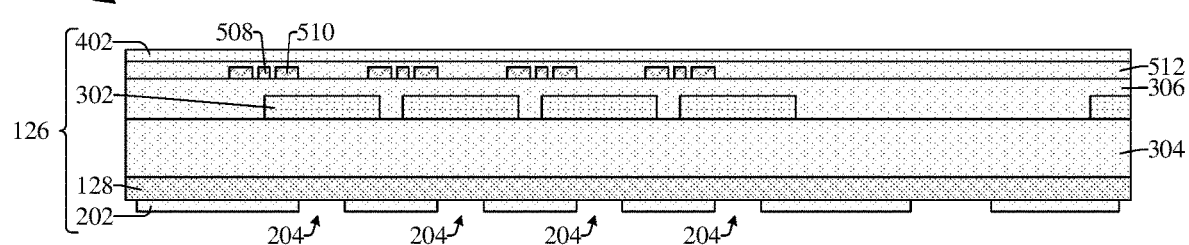

As shown in cross-sectional view 2600 of FIG. 26, a reflector layer 402 is deposited over the third dielectric layer 512. In some embodiments, the reflector layer 402 comprises aluminum, titanium, titanium nitride, chromium, or some other suitable material and is deposited by a CVD process, a PVD process, an ALD process, a sputtering process, an ELD process, an ECD process, or some other suitable process.

Figure 27:
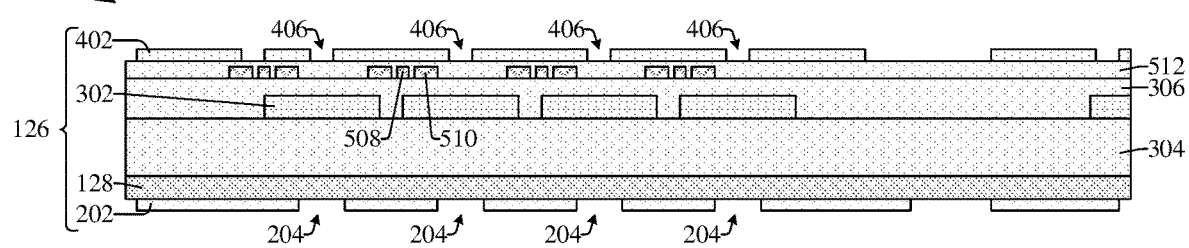

As shown in cross-sectional view 2700 of FIG. 27, the reflector layer 402 is patterned to form a plurality of apertures 406 in the reflector layer 402. The plurality of apertures 406 are delimited by sidewalls of the reflector layer 402. In some embodiments, the patterning comprises forming a masking layer (not shown) over the reflector layer 402 and etching the reflector layer 402 according to the masking layer to form the apertures 406 in the reflector layer 402. In some embodiments, the etching comprises a dry etching process or some other suitable process. In some embodiments, the masking layer may be removed during and/or after the etching.

Figure 28:
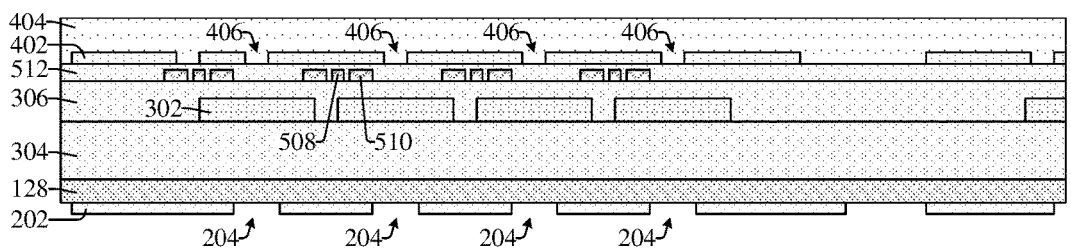

As shown in cross-sectional view 2800 of FIG. 28, a first clad layer 404 is deposited over the reflector layer 402 and between the sidewalls of the reflector layer 402 that delimit the apertures 406 in the reflector layer 402. In some embodiments, the first clad layer 404 comprises silicon dioxide or some other suitable material and is deposited by a CVD process, a PVD process, an ALD process, or some other suitable process.

Figure 29:
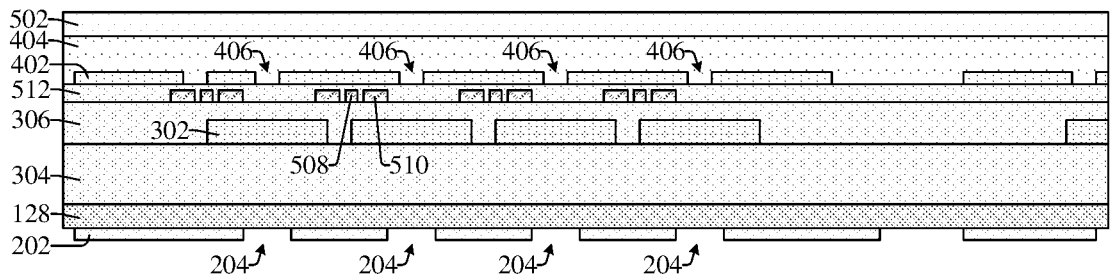

As shown in cross-sectional view 2900 of FIG. 29, a waveguide channel core layer 502 is deposited over the first clad layer 404. In some embodiments, the waveguide channel core layer 502 comprises BST, PZT, tantalum oxide, hafnium oxide, silicon nitride, aluminum oxide, or some other suitable material and is deposited by a CVD process, a PVD process, an ALD process, or some other suitable process.

Figure 30:
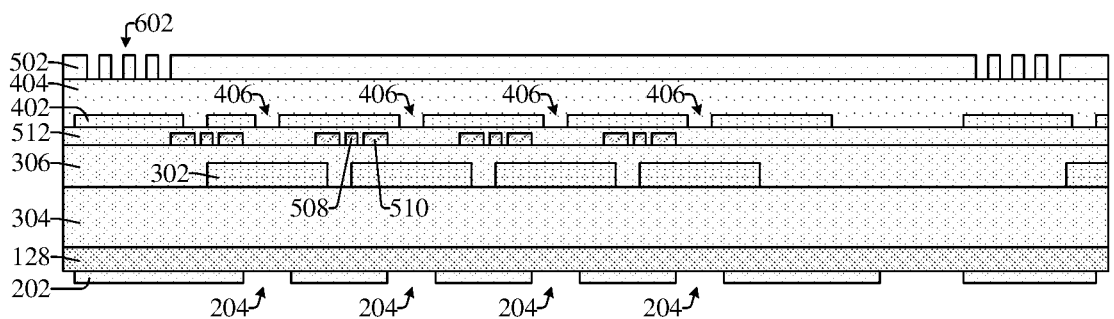

As shown in cross-sectional view 3000 of FIG. 30, the waveguide channel core layer 502 is patterned to form a light coupler structure 602 along the waveguide channel core layer 502. In some embodiments, the waveguide channel core layer 502 is also patterned to form a light splitter (not shown) along the waveguide channel core layer 502. In some embodiments, the patterning comprises forming a masking layer (not shown) over the waveguide channel core layer 502 and etching the waveguide channel core layer 502 according to the masking layer to form the light coupler structure 602 and/or the light splitter (not shown) along the waveguide channel core layer 502. In some embodiments, the etching comprises a dry etching process or some other suitable process. In some embodiments, the masking layer may be removed during and/or after the etching.

Figure 31:
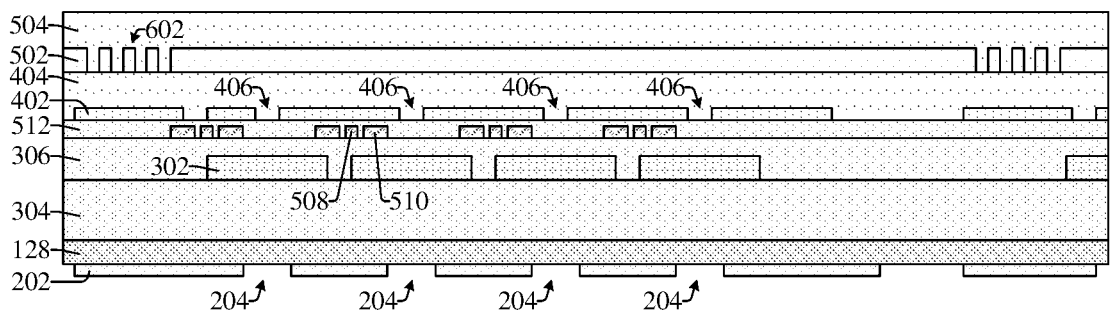

As shown in cross-sectional view 3100 of FIG. 31, a second clad layer 504 is deposited over the waveguide channel core layer 502 and between portions of the waveguide channel core layer 502 at the light coupler structure 602. In some embodiments, the second clad layer 504 comprises silicon dioxide or some other suitable material and is deposited by a CVD process, a PVD process, an ALD process, or some other suitable process. In some embodiments, a top surface of the second clad layer 504 is planarized (e.g., by way of a CMP process or some other suitable process) after the second clad layer 504 is deposited.

Figure 32:
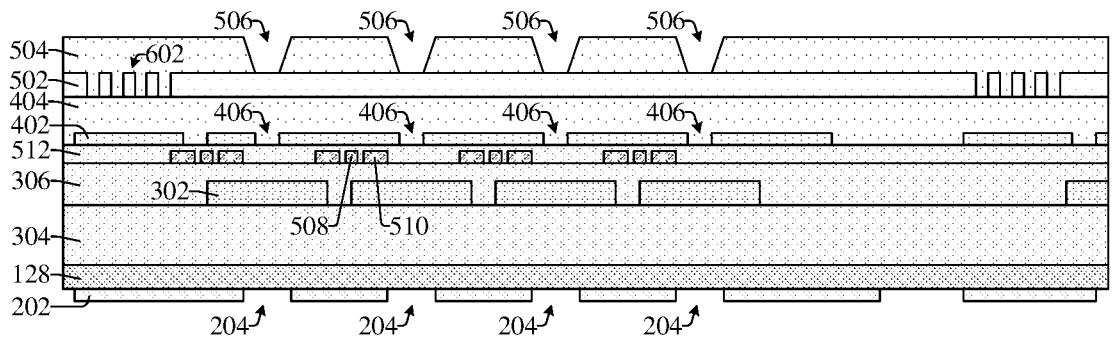

As shown in cross-sectional view 3200 of FIG. 32, the second clad layer 504 is patterned to form a plurality of bioreaction chambers 506 along the second clad layer 504 and directly over the apertures 406, the focusing layer segments of the focusing layer 302, and the apertures 204. The patterning uncovers portions of an upper surface of the waveguide channel core layer 502. The bioreaction chambers 506 are delimited by sidewalls of the second clad layer 504 and the portions of the upper surface of the waveguide channel core layer 502 that were uncovered by the patterning. In some embodiments, the patterning comprises forming a masking layer (not shown) over the second clad layer 504 and etching the second clad layer 504 according to the masking layer to form the bioreaction chambers 506 along the second clad layer 504. In some embodiments, the etching comprises a dry etching process or some other suitable process. In some embodiments, the masking layer may be removed during and/or after the etching.

Figure 33:
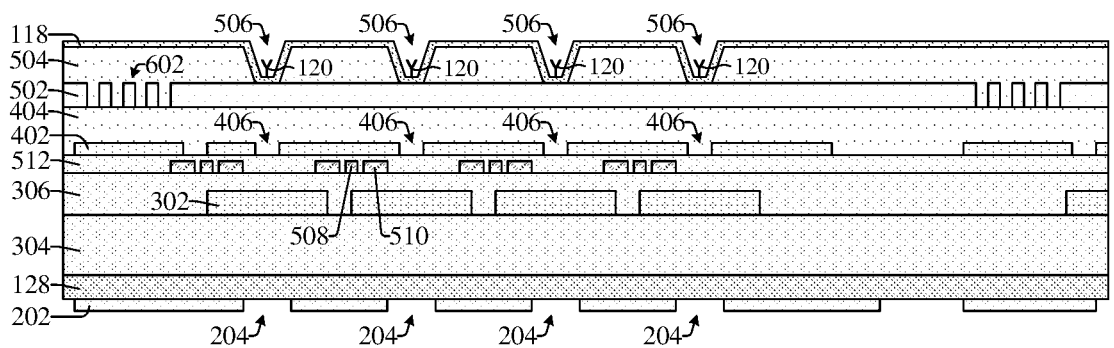

As shown in cross-sectional view 3300 of FIG. 33, a receptor layer 118 is formed on the second clad layer 504 and on the waveguide channel core layer 502 at the bioreaction chambers 506. For example, the receptor layer 118 is formed on the sidewalls of the second clad layer 504 and the portions of the upper surface of the waveguide channel core layer 502 that delimit the bioreaction chambers 506. In some embodiments, the receptor layer 118 is further formed on a top surface of the second clad layer 504.

In some embodiments, the receptor layer 118 comprises a hydrogel, a hydrophilic coating, or some other suitable material and is deposited on the second clad layer 504 and on the waveguide channel core layer 502 at the bioreaction chambers 506. In some other embodiments, the receptor layer 118 comprises a self-assembled monolayer (SAM) or the like which is formed on the second clad layer 504 and on the waveguide channel core layer 502 at the bioreaction chambers 506 by a SAM formation process.

In some embodiments, bioreceptors 120 are subsequently immobilized on the receptor layer 118 at the bioreaction chambers 506. In some other embodiments, the bioreceptors 120 may be immobilized at the bioreaction chambers 506 when a sample solution (e.g., 130 of FIG. 39) is provided to the bioreaction chambers 506 (see, for example, FIG. 39).

Figure 34:
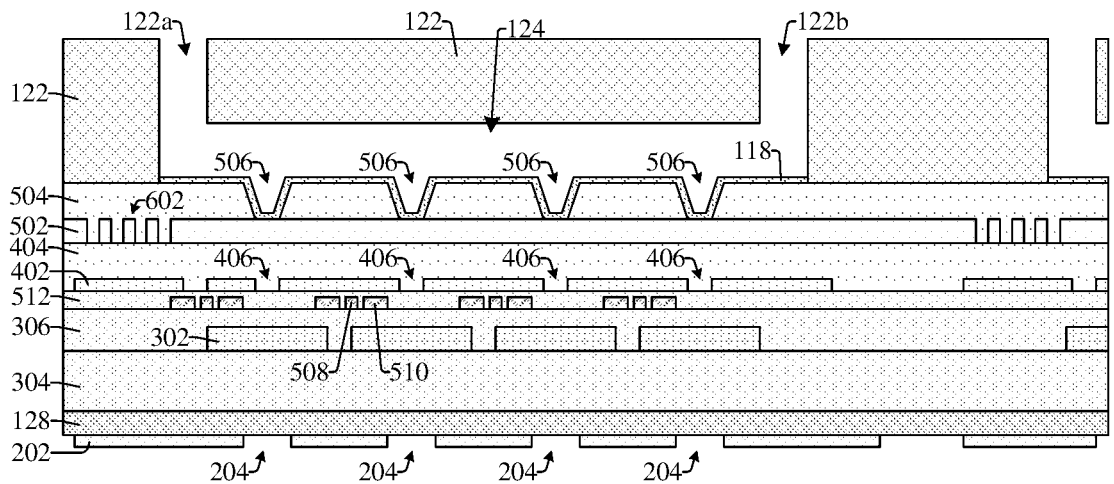

As shown in cross-sectional view 3400 of FIG. 34, a capping layer 122 is bonded over the second clad layer 504 to form a microfluidic channel 124 over the bioreaction chambers 506. In some embodiments, the capping layer 122 is bonded to the second clad layer 504. In some embodiments (not shown), the second clad layer 504 is bonded to an adhesive bonding layer (not shown) that is disposed on a top surface the second clad layer 504. In some embodiments (not shown), the receptor layer 118 is disposed directly between the capping layer 122 and the second clad layer 504 along the bonding interface.

In some embodiments, the bonding comprises a fusion bonding process, a plasma activated bonding process, a surface activated bonding process, an anodic bonding process, an adhesive bonding process, or some other suitable process. In some embodiments, the capping layer 122 comprises glass, quartz, polydimethylsiloxane (PDMS), polymethyl methacrylate (PMMA), some plastic material, or some other suitable material. In some embodiments, before the bonding, the capping layer 122 is patterned to form a capping recess (not labeled), the inlet 122a, and the outlet 122b in the capping layer.

Figure 35:
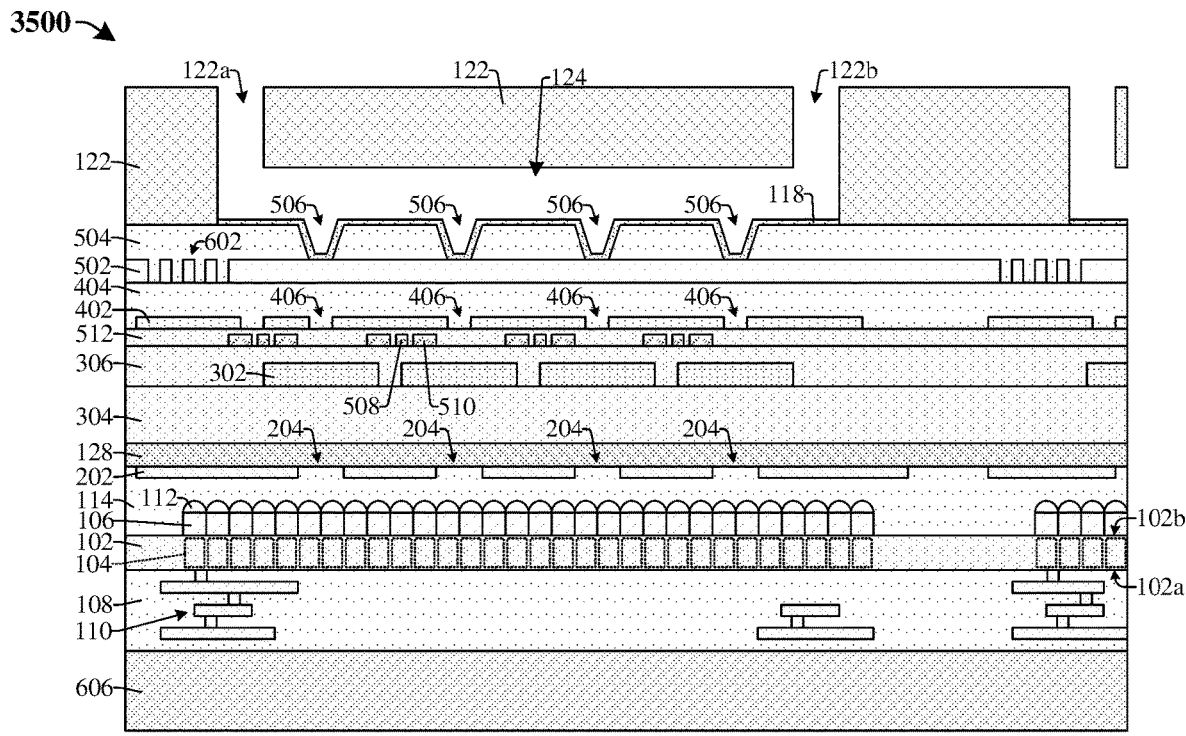

As shown in cross-sectional view 3500 of FIG. 35, the biosensor wafer (not labeled) is bonded over the image sensor wafer (not labeled). For example, the biosensor wafer is bonded to the image sensor wafer along the glue layer 114, the aperture layer 202, and the incident radiation filter layer 128. In some embodiments, the glue layer 114 comprises an epoxy configured to adhere to the aperture layer 202 and the incident radiation filter layer 128. In some embodiments, the bonding comprises an adhesive bonding process, a fusion bonding process, or some other suitable process. In some embodiments (e.g., in which the glue layer 114 is disposed around a periphery of the color filters 106 and the micro-lenses 112 but not directly over the micro-lenses 112), the glue layer 114, the aperture layer 202, and the incident radiation filter layer 128 are bonded along the periphery of the color filters 106 and the micro-lenses 112. In some embodiments, a cavity (not shown) comprising air or the like exists directly over the micro-lenses 112 and directly between the micro-lenses 112 and the aperture 202.

Figure 36:
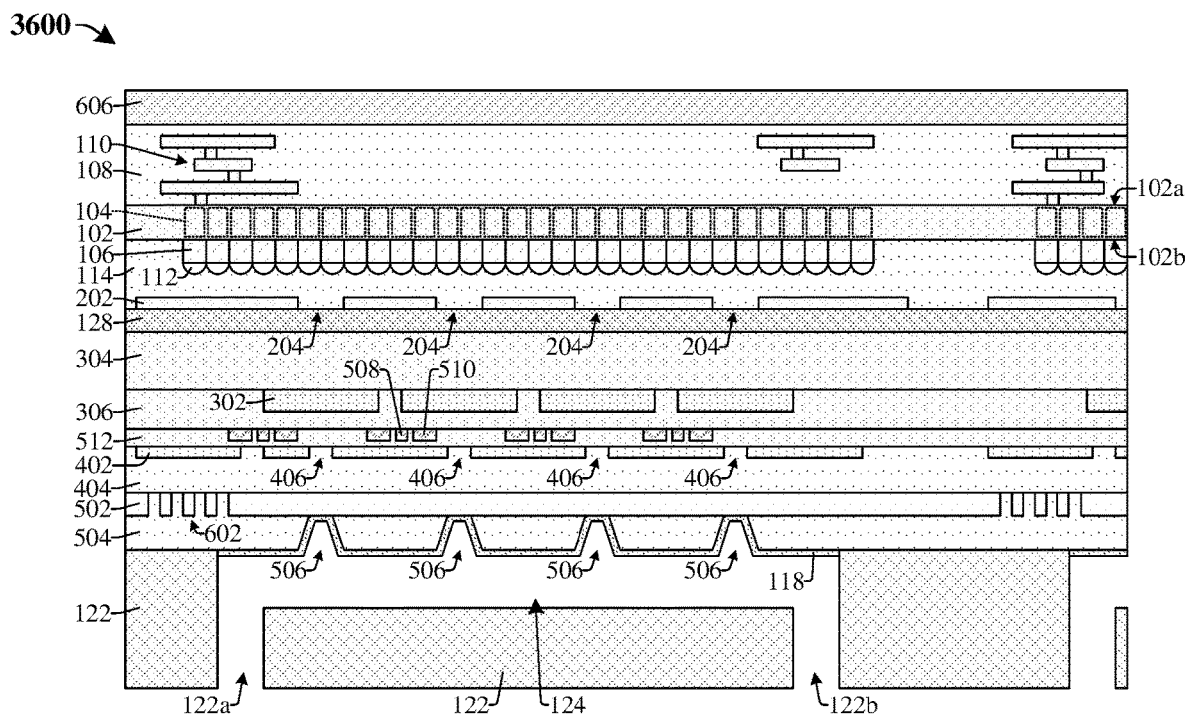

As shown in cross-sectional view 3600 of FIG. 36, the carrier wafer 606 is thinned along a second side of the carrier wafer 606, opposite the first side. In some embodiments, the thinning comprise a grinding process, an etch back process, a CMP process, or some other suitable process.

Figure 37:
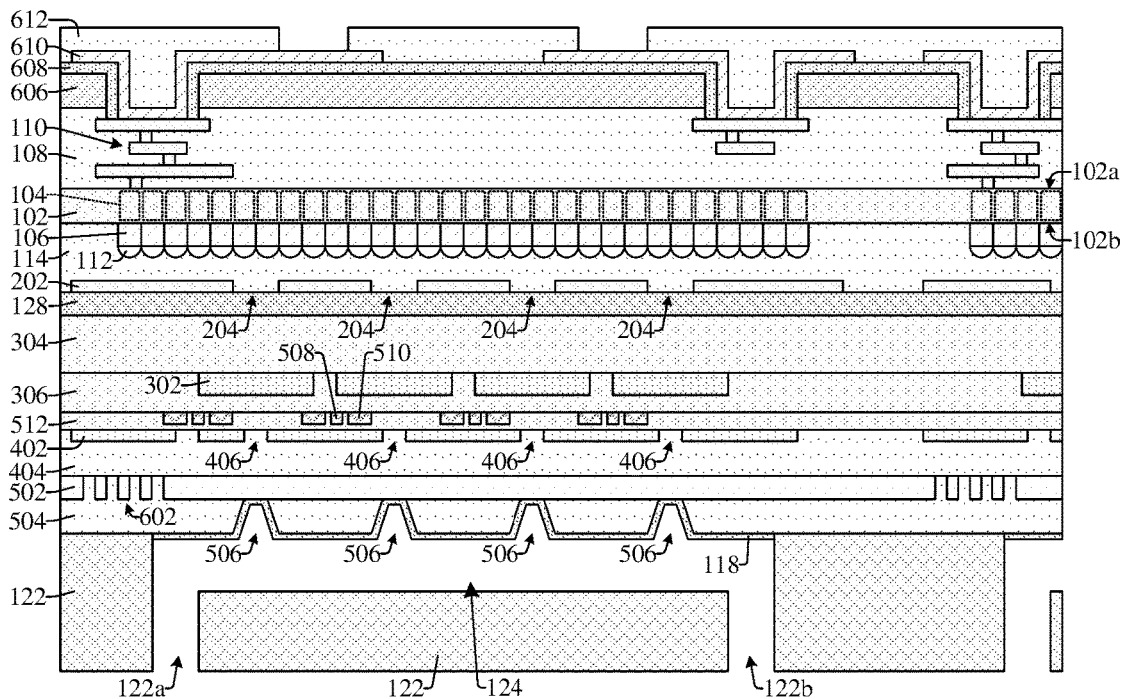

As shown in cross-sectional view 3700 of FIG. 37, a through-substrate via (TSV) structure comprising a TSV layer 610 is formed over the second side of the carrier wafer 606 such that the TSV layer 610 is coupled to conductive features of the interconnect structure 110. In some embodiments, forming the TSV structure comprises etching the carrier wafer 606 and the ILD structure 108 to form TSV openings (not shown) in the carrier wafer 606 and the ILD structure 108. The TSV openings uncover conductive features of the interconnect structure 110. An isolation layer 608 is deposited over the second side of the carrier wafer 606 and along the TSV openings. The isolation layer 608 is etched to remove the isolation layer 608 from the conductive features of the interconnect structure 110. The TSV layer 610 is deposited over the second side of the carrier wafer 606, along the TSV openings, and on the conductive features of the interconnect structure 110. The TSV layer 610 is etched to separate the TSV layer 610 in separate TSV segments. A passivation layer 612 is deposited over the TSV layer 610 and in remainders of the TSV openings to fill the TSV openings. The passivation layer 612 is etched to form passivation openings (not labeled) in the passivation layer 612. The passivation openings uncover portions of the TSV segments of the TSV layer 610.

Figure 38:
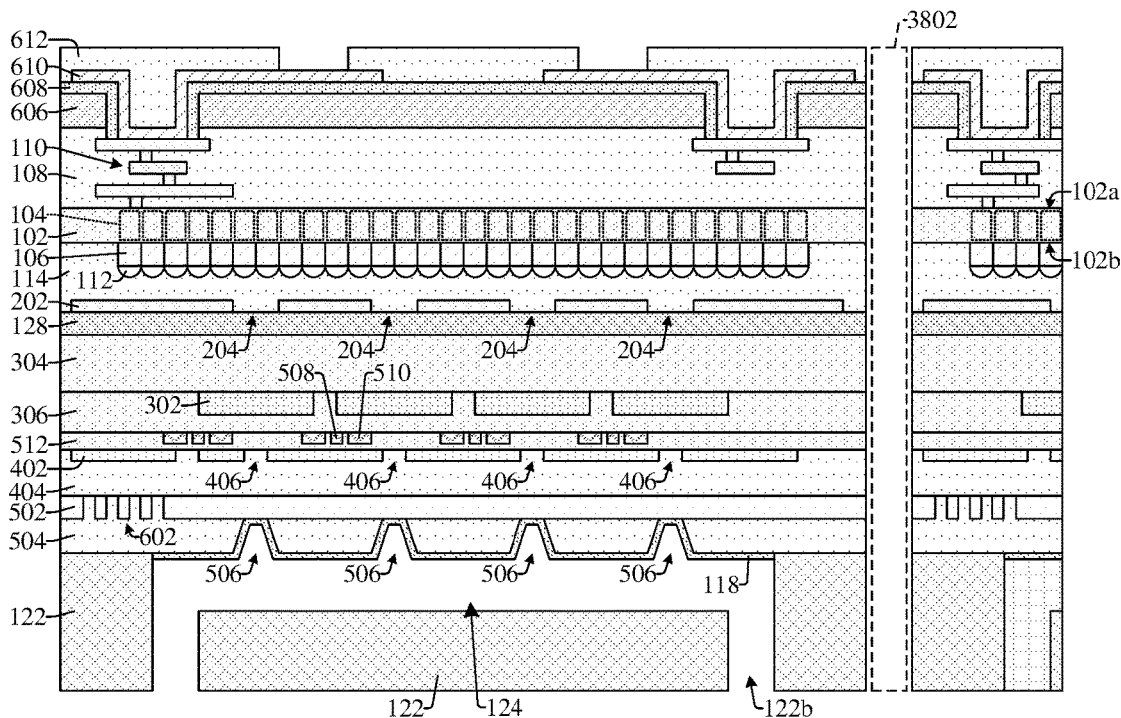

As shown in cross-sectional view 3800 of FIG. 38, a dicing process is performed along a scribe line 3802 to dice the bonded wafers into individual die. In some embodiments, the dicing process comprises bringing a dicing blade into contact with the wafers along the scribe line 3802 to cut through the wafers.

Figure 39:
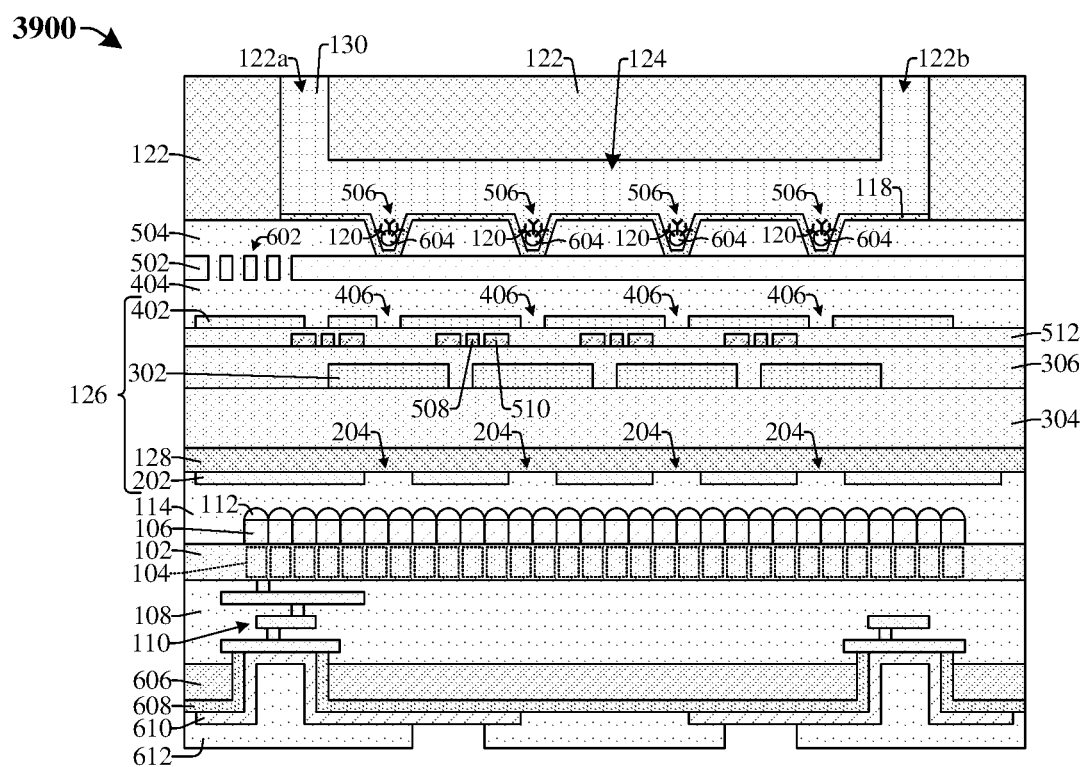

As shown in cross-sectional view 3900 of FIG. 39, in some embodiments, a sample solution 130 carrying microbeads 604 with bioreceptors 120 immobilized thereon is injected into the microfluidic channel 124 via the inlet 122a. In some embodiments, the sample solution 130 may also carry analytes (e.g., 132 of FIG. 6). In some other embodiments, a separate sample solution carrying the analytes is subsequently injected into the microfluidic channel 124 via the inlet 122a.

Figure 40:
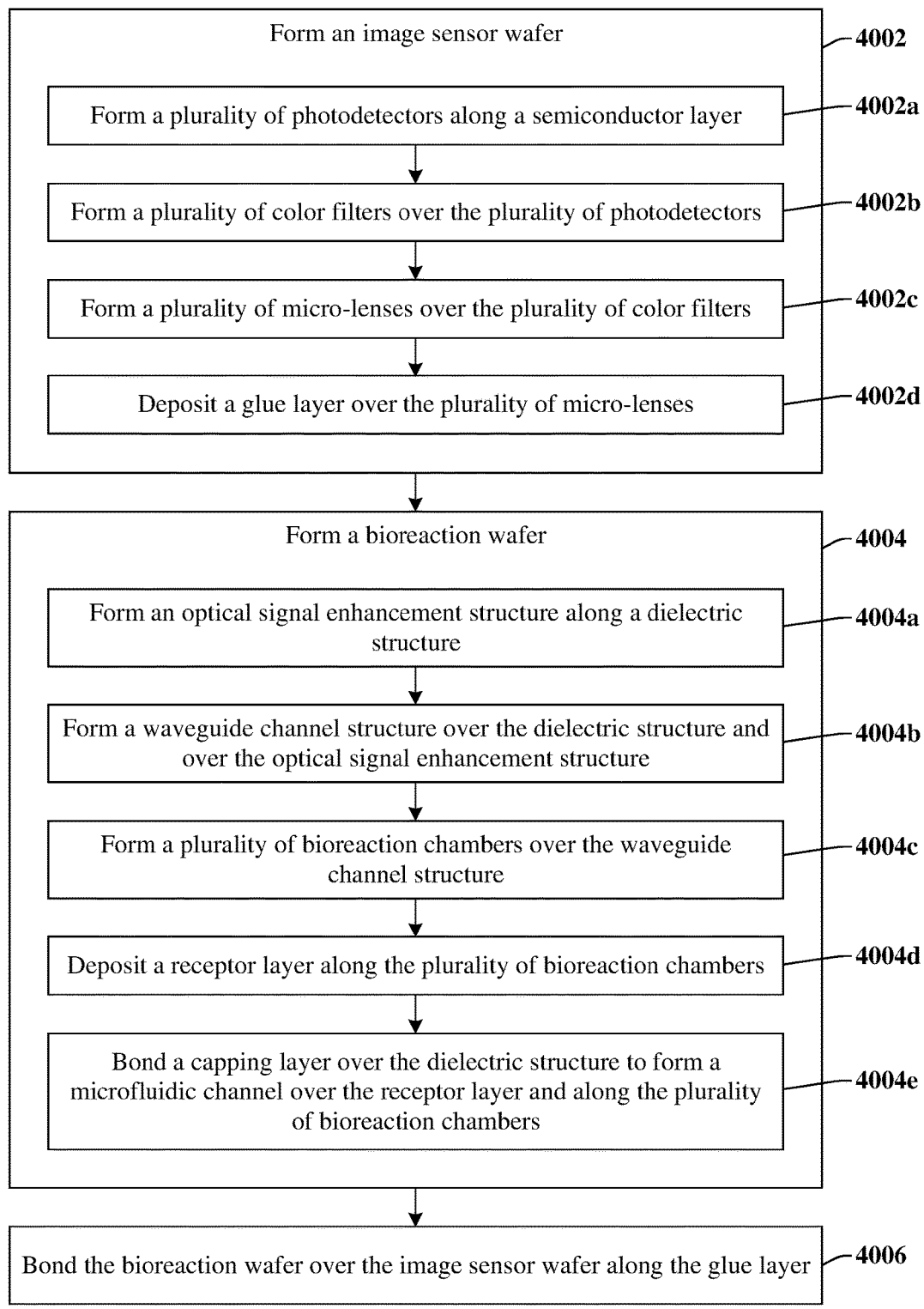
FIG. 40 illustrates a flow diagram of some embodiments of a method for forming an optical biosensor integrated chip.

FIG. 40 illustrates a flow diagram of some embodiments of a method 4000 for forming an optical biosensor integrated chip. While method 4000 is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At block 4002, form an image sensor wafer. In some embodiments, block 4002 comprises block 4002a, block 4002b, block 4002c, and block 4002d. FIGS. 11-16 illustrate cross-sectional views 1100-1600 of some embodiments corresponding to block 4002.

At block 4002a, form a plurality of photodetectors along a semiconductor layer. FIG. 11 illustrates a cross-sectional view 1100 of some embodiments corresponding to block 4002a.

At block 4002b, form a plurality of color filters over the plurality of photodetectors. FIG. 15 illustrates a cross-sectional view 1500 of some embodiments corresponding to block 4002b.

At block 4002c, form a plurality of micro-lenses over the plurality of color filters. FIG. 15 illustrates a cross-sectional view 1500 of some embodiments corresponding to block 4002c.

At block 4002d, deposit a glue layer over the plurality of micro-lenses. FIG. 16 illustrates a cross-sectional view 1600 of some embodiments corresponding to block 4002d.

At block 4004, form a bioreaction wafer. In some embodiments, block 4004 comprises block 4004a, block 4004b, block 4004c, block 4004d, and block 4004e. FIGS. 17-34 illustrate cross-sectional views 1700-3400 of some embodiments corresponding to block 4004.

At block 4004a, form an optical signal enhancement structure along a dielectric structure. FIGS. 17-27 illustrate cross-sectional views 1700-2700 of some embodiments corresponding to block 4004a.

At block 4004b, form a waveguide channel structure over the dielectric structure and over the optical signal enhancement structure. In some embodiments, forming the waveguide channel structure comprises depositing a first clad layer over the dielectric structure, depositing a waveguide channel core layer over the first clad layer, patterning the waveguide channel core layer (e.g., to form a light coupler, a light splitter, or the like along the waveguide channel core layer), and depositing a second clad layer over the patterned waveguide channel core layer. FIGS. 28-31 illustrate cross-sectional views 2800-3100 of some embodiments corresponding to block 4004b.

At block 4004c, form a plurality of bioreaction chambers over the waveguide channel structure. FIG. 32 illustrates a cross-sectional view 3200 of some embodiments corresponding to block 4004c.

At block 4004d, deposit a receptor layer along the plurality of bioreaction chambers. FIG. 33 illustrates a cross-sectional view 3300 of some embodiments corresponding to block 4004d. In some embodiments, method 4000 comprises immobilizing bioreceptors on the receptor layer at the bioreaction chambers during or after the deposition of the receptor layer. In some embodiments, method 4000 alternatively comprises injecting a sample solution carrying microbeads with bioreceptors immobilized thereon into the microfluidic channel after the bioreaction wafer and the image sensor wafer are bonded.

At block 4004e, bond a capping layer over the dielectric structure to form a microfluidic channel over the receptor layer and along the plurality of bioreaction chambers. In some embodiments, the microfluidic channel can be formed in the capping layer before the capping layer is bonded over the dielectric structure. FIG. 34 illustrates a cross-sectional view 3400 of some embodiments corresponding to block 4004e.

At block 4006, bond the bioreaction wafer over the image sensor wafer along the glue layer. FIG. 35 illustrates a cross-sectional view 3500 of some embodiments corresponding to block 4006.

In some embodiments, method 4000 further comprises forming an ILD structure and an interconnect structure within the ILD structure along the semiconductor layer. In some embodiments, method 4000 further comprises forming temperature sensors and/or heaters within the dielectric structure. In some embodiments, method 4000 further comprises forming a TSV layer along the ILD layer and contacting the interconnect structure. In some embodiments, method 4000 further comprises dicing the bonded wafers to separate the bonded wafers into individual die.

Thus, the present disclosure relates to an optical biosensor device comprising a bioreaction device integrated with an image sensor for improving a portability of the optical biosensor device.

Accordingly, in some embodiments, the present disclosure relates to an integrated chip including a semiconductor layer and a photodetector disposed along the semiconductor layer. A color filter is over the photodetector. A micro-lens is over the color filter. A dielectric structure comprising one or more dielectric layers is over the micro-lens. A receptor layer is over the dielectric structure. An optical signal enhancement structure is disposed along the dielectric structure and between the receptor layer and the micro-lens.

In other embodiments, the present disclosure relates to an integrated chip including a semiconductor layer. A plurality of photodetectors are disposed along the semiconductor layer. A plurality of color filters are over the plurality of photodetectors. A plurality of micro-lenses are over the plurality of color filters. A dielectric structure comprising one or more dielectric layers is over the plurality of micro-lenses. A first clad layer is over the dielectric structure. The first clad layer delimits a plurality of bioreaction chambers that are spaced apart along a top surface of the first clad layer. A receptor layer is over the first clad layer and lines the first clad layer at the plurality of bioreaction chambers. A capping layer is over the first clad layer and over the receptor layer. A microfluidic channel extends through the capping layer along a top surface of the receptor layer and along the plurality of bioreaction chambers. An optical signal enhancement structure is disposed between the plurality of bioreaction chambers and the plurality of photodetectors and is configured to enhance an optical signal emitted from bioreactions occurring along the plurality of bioreaction chambers.

In yet other embodiments, the present disclosure relates to a method for forming an integrated chip. The method includes forming a plurality of photodetectors along a semiconductor layer. A plurality of color filters are formed over the plurality of photodetectors, respectively. A plurality of micro-lenses are formed over the plurality of color filters, respectively. A glue layer is deposited over the plurality of micro-lenses. An optical signal enhancement structure is formed along a dielectric structure. A plurality of bioreaction chambers are formed over the dielectric structure and over the optical signal enhancement structure. A receptor layer is deposited along the plurality of bioreaction chambers. A capping layer having a microfluidic channel therein is bonded over the receptor layer and over the plurality of bioreaction chambers. The dielectric structure is bonded over the plurality of photodetectors and along the glue layer such that the plurality of bioreaction chambers are disposed over the plurality of photodetectors.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for forming an integrated chip, the method comprising:
   forming a plurality of photodetectors along a semiconductor layer;
   forming a plurality of color filters over the plurality of photodetectors, respectively;

forming a plurality of micro-lenses over the plurality of color filters, respectively;
depositing a glue layer over the plurality of micro-lenses;
forming an optical signal enhancement structure along a dielectric structure;
forming a plurality of bioreaction chambers over the dielectric structure and over the optical signal enhancement structure;
depositing a receptor layer along the plurality of bioreaction chambers;
bonding a capping layer having a microfluidic channel therein over the receptor layer and over the plurality of bioreaction chambers; and
bonding the dielectric structure over the plurality of photodetectors and along the glue layer such that the plurality of bioreaction chambers are disposed over the plurality of photodetectors.

2. The method of claim 1, wherein forming the optical signal enhancement structure comprises:
depositing an incident radiation filter layer on a backside of the dielectric structure;
depositing an aperture layer on the incident radiation filter layer;
patterning the aperture layer to form a plurality of first apertures in the aperture layer;
forming a focusing layer comprising a plurality of focusing segments within the dielectric structure;
depositing a reflector layer over the dielectric structure; and
patterning the reflector layer to form a plurality of second apertures in the reflector layer.

3. The method of claim 2, further comprising:
forming a temperature sensor and a heater within the dielectric structure.

4. The method of claim 1, further comprising:
depositing a first clad layer over the dielectric structure; and
depositing a waveguide channel core layer over the first clad layer;
patterning the waveguide channel core layer to form a light coupler structure along the waveguide channel core layer; and
depositing a second clad layer over the waveguide channel core layer.

5. The method of claim 4, wherein the plurality of bioreaction chambers are formed by patterning the second clad layer, and wherein the plurality of bioreaction chambers are delimited by sidewalls of the second clad layer and an upper surface of the waveguide channel core layer.

6. A method of forming an integrated chip, the method comprising:
forming a plurality of photodetectors along a semiconductor layer;
forming a plurality of color filters over the plurality of photodetectors;
forming a plurality of micro-lenses over the plurality of color filters;
forming an optical signal enhancement structure along a dielectric structure;
depositing a first clad layer over the optical enhancement structure;
etching the first clad layer to form a plurality of bioreaction chambers spaced apart along a top surface of the first clad layer;
depositing a receptor layer over the first clad layer and lining the first clad layer at the plurality of bioreaction chambers;
bonding a capping layer over the first clad layer and over the receptor layer, wherein a microfluidic channel extends through the capping layer along a top surface of the receptor layer and along the plurality of bioreaction chambers; and
bonding the dielectric structure, first clad layer, receptor layer, and capping layer over the plurality of photodetectors,
wherein the optical signal enhancement structure is between the plurality of bioreaction chambers and the plurality of photodetectors and configured to enhance an optical signal emitted from bioreactions occurring along the plurality of bioreaction chambers.

7. The method claim 6, wherein forming the optical signal enhancement structure comprises:
forming an incident radiation filter layer on a bottom surface of the dielectric structure so that incident radiation filter layer is between the dielectric structure and the micro-lenses.

8. The method of claim 7, wherein forming the optical signal enhancement structure further comprises:
depositing an aperture layer along a bottom of the incident radiation filter layer;
etching the aperture layer to form a plurality of first apertures in the aperture layer; and
depositing a glue layer over the plurality of micro-lenses so that the glue layer is between the aperture layer and the plurality of micro-lenses, wherein portions of the glue layer fill the plurality of first apertures, and wherein the portions of the glue layer are directly under the plurality of bioreaction chambers.

9. The method of claim 8, wherein forming the optical signal enhancement structure further comprises:
forming a focusing layer within the dielectric structure; and
etching the focusing layer to form a plurality of focusing segments from the focusing layer, the plural of focusing segments directly below the plurality of bioreaction chambers, respectively.

10. The method of claim 9, wherein forming the optical signal enhancement structure further comprises:
depositing a second clad layer over the dielectric structure, wherein the second clad layer is between the first clad layer and the dielectric structure; and
depositing a waveguide channel core layer over the second clad layer, wherein the waveguide channel core layer is between the first clad layer and the second clad layer, wherein the bioreaction chambers are directly over a top surface of the waveguide channel core layer.

11. The method of claim 10, further comprising:
depositing a reflector layer over the focusing layer, wherein the reflector layer is disposed along a top surface of the dielectric structure and a bottom surface of the second clad layer, wherein the reflector layer has a plurality of second apertures therein, wherein the second clad layer is over the reflector layer, wherein portions of the second clad layer fill the plurality of second apertures, and wherein the portions of the second clad layer are directly under the plurality of bioreaction chambers.

12. A method for forming an integrated chip, the method comprising:
forming a plurality of photodetectors along a semiconductor layer;
forming a plurality of color filters over the plurality of photodetectors, respectively;

forming a plurality of micro-lenses over the plurality of color filters, respectively;

depositing a glue layer over the plurality of micro-lenses;

forming an optical signal enhancement structure along a dielectric structure, wherein forming the optical signal enhancement structure comprises forming a radiation filter layer under the dielectric structure;

forming a plurality of bioreaction chambers over the dielectric structure and over the optical signal enhancement structure;

depositing a receptor layer along the plurality of bioreaction chambers;

bonding a capping layer having a microfluidic channel therein over the receptor layer and over the plurality of bioreaction chambers; and bonding the radiation filter layer and the dielectric structure over the plurality of photodetectors and along the glue layer such that the plurality of bioreaction chambers are disposed over the plurality of photodetectors.

13. The method of claim 12, wherein forming the optical signal enhancement structure comprises forming an aperture layer on the radiation filter layer.

14. The method of claim 12, wherein forming the optical signal enhancement structure comprises forming a plurality of focusing layer segments within the dielectric structure.

15. The method of claim 12, wherein forming the optical signal enhancement structure comprises forming a reflector layer over the dielectric structure.

16. The method of claim 12, further comprising:
forming a temperature sensor within the dielectric structure.

17. The method of claim 12, further comprising:
forming a heater within the dielectric structure.

18. The method of claim 12, further comprising:
forming a waveguide layer over the dielectric structure and over the optical signal enhancement structure, wherein the plurality of bioreaction chambers are formed along the waveguide layer, and wherein the receptor layer is deposited on the waveguide layer.

19. The method of claim 18, further comprising:
forming a light coupler structure along the waveguide layer.

20. The method of claim 12, wherein the microfluidic channel extends through the capping layer along the receptor layer and the plurality of bioreaction chambers.

* * * * *